(12) United States Patent
Rybak et al.

(10) Patent No.: US 7,029,899 B1
(45) Date of Patent: Apr. 18, 2006

(54) SELECTIVE TOXICITY OF AMINO-TERMINAL MODIFIED RNASE A SUPERFAMILY POLYPEPTIDES

(75) Inventors: Susanna M. Rybak, Frederick, MD (US); Dianne L. Newton, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 09/807,556

(22) PCT Filed: Nov. 1, 1999

(86) PCT No.: PCT/US99/25737

§ 371 (c)(1),
(2), (4) Date: Jul. 30, 2001

(87) PCT Pub. No.: WO00/26233

PCT Pub. Date: May 11, 2000

Related U.S. Application Data

(60) Provisional application No. 60/106,732, filed on Nov. 2, 1998.

(51) Int. Cl.
*A61K 38/46* (2006.01)
*C12N 15/54* (2006.01)
*C12N 15/62* (2006.01)
*C12N 15/00* (2006.01)
*C07H 21/04* (2006.01)

(52) U.S. Cl. ............... 435/199; 435/195; 435/536; 435/23.4; 435/69.7; 424/94.61; 424/183.1; 530/350; 530/391.7; 536/23.2

(58) Field of Classification Search ............... 435/199, 435/195, 69.7; 424/94.61, 183.1; 530/350, 530/391.7; 536/23.2, 23.4
See application file for complete search history.

(56) References Cited

OTHER PUBLICATIONS

Rosenberg H. et al Molecular Cloning of the Humaneosinophil-derived neurotoxin: A member of the Ribonuclease family. Proc. Natl. Acad. Sci. USA vol. 86, pp. 4460-4464, 1989.*
Beintema JJ et. al., Amino acid sequence of the nonsecretory ribonuclease of human urine. Biochemistry 27, 4530-4538, 1988.*
Sakakibara et al. A putative mouse oocyte maturation inhibitory protein from urine of pregnant women: N-terminal sequence homology with human nonsecretory ribonuclease. Chem. Pharm. Bull. 1991, 39(1) 146-149.*
Barker et al., Eosinophile Cationic Protein cDNA, Comparison with other toxic Cationic Proteins and Ribonucleases 1989. The journal of immunology vol. 143, 952-955.*
Sakakibara et al., Characterization of a unique Nonsecretory Ribonuclease from urine of Pregnant woman 1992. J. Biochemistry, 111, 325-330.*
Beintema, J., et al., "Amino Acid Sequence of the Nonsecretory Ribonuclease of Human Urine," *Biochemistry*, 1988, pp. 4530-4538, vol. 27, American Chemical Society.
Beintema, et al., "Molecular Evolution of the Ribonuclease Superfamily," *Prog. Biophys. Mol. Biol.*, 1988, p. 165-190, vol. 51.
Beintema, J., et al., "The Ribonuclease A Superfamily: general discussion," *Cell Mol. Life Sci.*, 1998, pp. 825-832, vol. 54.
Boix, E., et al., "Role of the N Terminus in RNase a Homologues: Differences in Catalytic Activity, Ribonuclease Inhibitor Interaction and Cytotoxicity," *J. Mol. Biol.*, 1996, pp. 992-1007, vol. 257, Academic Press Limited.
Cara, A., et al., "Inhibition of HIV-1 replication by combined expression of gag dominant negative mutant and a human ribonuclease in a tightly controlled HIV-1 inducible vector," *Gene Therapy*, 1998, pp. 65-75, vol. 5, Stockton Press.
Fodstad, et al., "Phase I Study of the Plant Protein Ricin," *Cancer Res.*, 1984, p. 862, vol. 44.
Griffiths, S., et al., "Ribonuclease inhibits Kaposi's sarcoma," *Nature*, Dec. 11, 1997, p. 568, vol. 390.
Gullberg, et al., "The Cytotoxic Eosinophil Cationic Protein (ECP) Has Ribonuclease Activity," *Biophys. Biochem. Res. Comm.*, 1986, pp. 1239-1242, vol. 139, No. 3, Academic Press, Inc.
Lunardi-Iskandar, Y., et al., "Effects of a urinary factor from women in early pregnancy on HIV-1, SIV and associated disease," *Nature Medicine*, Apr. 1998, pp. 428-434, vol. 4, No. 4.

(Continued)

*Primary Examiner*—Rebecca E. Prouty
*Assistant Examiner*—Kagnew Gebreyesus
(74) *Attorney, Agent, or Firm*—Townsend and Townsend and Crew LLP

(57) ABSTRACT

This invention provides RNase A superfamily polypeptides with modified amino terminal which can be used to selectively kill target Kaposi's sarcoma cells, neoplastic endothelial cells, and non-neoplastic endothelial cells. In certain embodiments of the invention, the amino terminal modification consists of an addition of 4 amino acid sequence consisting of the SLHV sequence at position −4 to −1 to the eosinophil derived neurotoxin protein. The amino terminal addition is capable of directing the claimed RNase A superfamily polypeptides to proliferating endothelial cells, such as Kaposi's sarcoma cells, and selectively killing these cells.

10 Claims, 8 Drawing Sheets

OTHER PUBLICATIONS

Newton, D.L., et al., "Expression and characterization of a cytotoxic human-frog chimeric ribonuclease: potential for cancer therapy," *Protein Eng.*, 1997, pp. 463-470, vol. 10, Oxford University Press.

Newton, D.L., et al., "Single Amino Acid Substitutions at the N-Terminus of a Recombinant Cytotoxic Ribonuclease Markedly Influence Biochemical and Biological Properties," *Biochemistry*, 1998, pp. 5173-5183, vol. 37, American Chemical Society.

Preuss, et al., "Cloning of cDNA encoding the complete precursor for bovine seminal ribonuclease," *Nuc. Acids. Res.*, 1990, p. 1057, vol. 18, Oxford University Press.

Rosenberg, H., et al., "Molecular cloning of the human eosinophil-derived neurotoxin: A member of the ribonuclease gene family," *Proc. Natl. Acad. Sci. USA*, Jun. 1989, p. 4460, vol. 86.

Rosenberg, et al., "Human Eosinophil Cationic Protein: Molecular Cloning of a Cytotoxin and Helminthotoxin with Ribonuclease Activity," *J. Exp. Med.*, Jul. 1989, p. 163-176, vol. 170, The Rockefeller University Press.

Rosenberg, et al., "Eosinophil Cationic Protein and Eosinophil-derived Neurotoxin: Evolution of Novel Function in a Primate Ribonuclease Gene Family," *J. Biol. Chem.*, 1995, pp. 21539-21544, vol. 270, No. 37, USA.

Rybak, S.M., et al., "RNase and RNase immunofusions for cancer therapy," *Tumor Targeting*, 1995, pp. 141-147, vol. 1.

Sakakibara, R., et al., "A Putative Mouse Oocyte Maturation Inhibitory Protein from Urine of Pregnant Women: N-Terminal Sequence Homology with Human Nonsecretory Ribonuclease," *Chem. Pharm. Bull.*, 1991, pp. 146-149, vol. 39., No. 1, Pharmaceutical Society of Japan.

Slifman, et al., "Ribonuclease Activity Associated with Human Eosinophil-Derived Neurotoxin and Eosinophil-Derived Neurotoxin and Eosinophil Cationic Protein," *J. Immunol. Comm.*, 1986, pp. 2913-2917, vol. 137, No. 9, The American Association of Immunologists, USA.

Titani, et al, "Amino Acid Sequence of Sialic Acid Binding Lectin from Frog (*Rana catesbeiana*) Eggs," *Biochemistry*, 1987, p. 2189, vol. 26, the American Chemical Society.

Youle, R., et al., "Cytotoxic Ribonucleases and Chimeras in Cancer Therapy," *Critical Reviews in Therapeutic Drug Carrier Systems*, 1993, pp. 1-28, vol. 10, No. 1, CRC Press, Inc.

Zewe, et al., "Cloning and cytotoxicity of a human pancreatic RNase immunofusion," *Immuno Technology*, pp. 127-136, vol. 3, Elsevier Science B.V.

* cited by examiner

```
                1                *                                        *   50
FROG LECTIN  .....anwat  FqqkHi.int  piin....Cn  tiMdnniyiv  ggqCKrvNTF
  ONCONASE   .....adwlt  FqkkHi.int  rdvd....Cd  niMstnlf..  ..hCKdkNTF
       EDN   kppqftwaqw  FetqHinmts  qq......Ct  naMqvinnyq  rr.CKnqNTF
       ECP   rppqftraqw  FaiqHislnp  pr......Ct  iaMrainnyr  wr.CKnqMTF
       ANG   laqddyryih  FltqHyd.ak  pkgrndeyCf  hmMknrrltr  p..CKdrNTF
   SEMINAL   ..kes.aaak  FerqHmdsgn  spssssnyCn  lmMccrkmtq  gk.CKpvNTF
   RNASE A   ..ket.aaak  FerqHmdsst  saasssnyCn  qmMksrnltk  dr.CKpvNTF 51                                                      100
FROG LECTIN  iissattvka  iCtgvi..nm  nvl.......  SttrfqlntC  trts...itp
  ONCONASE   iysrpapvka  iCkgii.ask  nvlt.....t  Sefy..lsdC  ......nvts
       EDN   llttfanvvn  VCgnpnmtcp  snktrknchh  SgsqvplihC  nlttpspqni
       ECP   lrttfanvvn  vCgnqsircp  hnrtlnnchr  SrfrvpllhC  dlinpgaqni
       ANG   ihgnkndika  iCedrngqpy  rg....dlri  SksefqitiC  khkggs..sr
   SEMINAL   vhesladvka  vCsqkkvtck  ngqt..ncyq  SkstmritdC  ret..gssky
   RNASE A   vhesladvqa  vCsqknvack  ngqt..ncyq  SkstmsitdC  ret..gssky 101                                  *                  150
FROG LECTIN  rpCpYssrta  tnyicVkCen  q.........  ..yPVHfagi  grcp......
  ONCONASE   rpCkYklkks  tnkfcVkCen  q.........  ..aPVHfvgv  gsc.......
       EDN   snCrYaqtpa  nmfyiVaCdn  rdqrrdppqy  pvvPVHldri  i.........
       ECP   snCrYadrpg  rrfyvVaCdn  rd.prdspry  pvvPVHldtt  i.........
       ANG   ppCrYgated  srvivVgCan  g.........  ..lPVHfdes  fitprh....
   SEMINAL   pnCaYkttqv  ekhiiVaCgg  k.........  psvPVHfdas  v.........
   RNASE A   pnCaYkttqa  nkhiiVaCeg  n.........  pyvPVHfdas  v.........
```

FIG. 1.

r EDN         M K P P Q F T W A Q W F (-4)r EDN   M S L H V K P P Q F T W A Q W F

-4      -1 +1                    10

SELECTIVE TOXICITY OF AMINO-TERMINAL MODIFIED RNASE A SUPERFAMILY POLYPEPTIDES

CROSS-REFERENCES TO RELATED APPLICATIONS

This application claims the benefit of U.S. Provisional Patent application Ser. No. 60/106,732, filed on Nov. 2, 1998, the teachings of which are herein incorporated by reference.

STATEMENT AS TO RIGHTS TO INVENTIONS MADE UNDER FEDERALLY SPONSORED RESEARCH AND DEVELOPMENT

Not applicable.

FIELD OF INVENTION

This invention provides RNase A superfamily polypeptides with modified amino termini which can be used to selectively kill target Kaposi's sarcoma cells, neoplastic endothelial cells, and non-neoplastic endothelial cells. In certain embodiments of the invention, the amino terminal modification consists of an addition of 4 amino acid sequence consisting of the SLHV sequence at position −4 to −1 to the EDN protein. The amino terminal addition is capable of directing the claimed RNase A superfamily polypeptide to proliferating endothelial cells, such as Kaposi's sarcoma cells, and selectively killing these cells.

BACKGROUND OF THE INVENTION

AIDS and Kaposi's Sarcoma

Treatment of cancers is an area of clinical medicine that is of vital importance, but yet remains fraught with complications and suboptimal results. There are various cancer treatments such as surgery, chemotherapy, and radiation therapy. Most of these treatments have serious side effects because of lack of specificity of the treatments.

Acquired Immunodeficiency Syndrome (AIDS) has become a serious and deadly epidemic that has claimed the lives of thousands of people. Currently, there are no completely effective vaccines to cure AIDS. The most common malignancy found in patients with AIDS is Kaposi's sarcoma (KS). The AIDS related form of Kaposi's sarcoma most frequently presents with cutaneous lesions. Mucosal involvement of the oral cavity is the second most common site of the disease. The tumor lesions are noted frequently on the palate and gums, and can cause tooth loss. See Paredes, J., *J. Acquir. Immune. Defic. Syndr. Hum. Retriviral,* 9(2): 138–144, 1995, which is herein incorporated by reference. Nearly every organ can be affected with Kaposi's sarcoma, including liver, lung, spleen, pancreas, and heart, etc.

Kaposi's sarcoma is a multifocal neoplasm, consisting of several cell types and angiogenesis. The tumor is usually considered to be of endothelial origin (Rutgers et al., *Am. J. Pathol.* 122: 493–499, 1986). Even though there have been attempts in curing Kaposi's sarcoma, current Kaposi's sarcoma treatments can cause serious side effects such as myelotoxicity and neurotoxicity. See Northfeldt, et al., *Hematology/Oncology Clinics of North America* 5: 297–310, 1991, which is incorporated herein by reference. Existing Kaposi's sarcoma treatments can induce immunosuppression, and thus can worsening the pre-existing immunodeficiency that is usually present in AIDS patients. In 1995, it was discovered that the growth of Kaposi's sarcoma derived cell lines was inhibited in vitro and in vivo by a human pregnancy hormone purified from urine, the human chorionic gonadotropin (hCG). Lunardi-Iskandar, Y., et al., *Nature* 375: 64–68, 1995. Later, researchers found that the active ingredient was not hCG, but instead it may have been contaminating hCG-associated factors that exhibit anti-KS activities. However, the precise nature of these factors is not known in the art at the present time, and there exists a great need to find the compound that inhibits the growth of KS cancer cells.

The RNase A Superfamily: Antitumor Agents, Sequence Homology.

The Ribonuclease A superfamily is consisted of ribonucleases that are endonucleases, and are homologous to each other in sequence. They have long been known to be cytotoxic agents during host defense and physiological cell death pathway. Roth, J. *Cancer Res.* 23: 657–666, 1963. As early as 1955, it was discovered that bovine pancreatic RNase A had anticancer properties when injected into mice tumor models. See Ledoux, L., *Nature,* 176: 36, 1955. Later, bovine seminal RNase, a member of the RNase A superfamily, and closely homologous to bovine pancreatic RNase A, was found to be toxic to mammalian cells in a number of systems. See Vescia, S. and Tramontano, D., *Mol. Cell. Biochem.,* 36: 125, 1981. The bovine seminal RNase was also found to be active in extending the survival rate in tumor models. See Laccetti, O., et al., *Cancer Res.,* 52: 4582, 1992.

Among the RNase A superfamily members, eosinophil derived neurotoxin protein (EDN) has been identified as a neurotoxin, along with other human RNases, such as eosinophil cationic protein (ECP). Both EDN and ECP are homologous to RNase A in about 35% of their amino acid sequences. Cytotoxic eosinophil proteins have been reported to have RNase activity (Slifman, et al., *J. Immunol. Comm.,* 137(9): 2913–2917, 1986; Gullberg, et al., *Biophys. Biochem. Res. Comm.,* 139(3): 1239–1242, 1986). The sequence of human EDN was found to be identical to that of the nonsecretory ribonuclease from human urine (Beintema, et al., *Biochemistry,* 27: 4530–4538, 1988). It was recently discovered that EDN polypeptides are also potent inhibitors of cell-free protein synthesis (Zewe, et al., *Immuno Technology* 3:127–136).

The N-terminus of the RNase A superfamily polypeptides is important for expression of their cytotoxic properties. See, Boix, E., et al., *J. Mol. Biol.,* 257: 992–1007, 1996; Newton, D. L., et al., *Protein Eng.* 10: 463–470, 1997; Newton, D. L., et al., *Biochemistry* 37: 5173–5183, 1998. It was recently discovered that a protein isolated from the urine of pregnant women which is homologous to the N-terminal sequence of EDN shows inhibitory effect on the development of mouse oocytes in culture. Sakakibara, R., et al., *Chem. Pharm. Bull.* 39: 146–149, 1991.

The present invention is based upon the discovery that RNase A superfamily polypeptides which are modified at the amino terminal by adding a short amino acid sequence are effective in directing the cytotoxic activity of the RNase to cancerous endothelial cells. This discovery provides promising treatments for cancers, such as Kaposi's sarcoma.

SUMMARY OF THE INVENTION

This invention provides an RNase A superfamily polypeptide having an N-terminus of the sequence: $X^1X^2SLX^3V$, wherein $X^1$ represents methionine or is absent, $X^2$ represents glycine or is absent, and $X^3$ represents an amino acid residue (SEQ ID NO:9), said RNase A superfamily polypeptide being selectively toxic to a proliferating endothelial cell.

In a preferred embodiment, the invention provides an RNase A superfamily polypeptide having the sequence of SEQ ID NO:2. In another preferred embodiment, the invention provides an RNase A superfamily polypeptide having 90% homology to SEQ ID NO:2. In yet another preferred embodiment, the invention provides an RNase A superfamily polypeptide having the sequence of SEQ ID NO:4. In a further preferred embodiment, the invention provides an RNase A superfamily polypeptide having 90% homology to SEQ ID NO:4. More preferably, the RNase A superfamily polypeptide has a N-terminus which is MGSLHV (SEQ ID NO:10). Most preferably, the invention provides an RNase A superfamily polypeptide wherein the N-terminus is MSLHV (SEQ ID NO:11), and the rest of the polypeptide includes the EDN amino acid sequence.

In another aspect, the invention provides an RNase A superfamily polypeptide which is selectively toxic to a proliferating endothelial cell that is neoplastic. The invention also provides an RNase A superfamily polypeptide which is selectively toxic to a proliferating endothelial cell that is non-neoplastic. Preferably, the invention provides an RNase A superfamily polypeptide which is selectively toxic to a neoplastic endothelial cell which is Kaposi sarcoma KS Y-1 cell.

In yet another aspect, the invention provides a pharmaceutical composition comprising a unit dosage RNase A superfamily polypeptide comprising an N-terminus of the sequence: $X^1X^2SLX^3V$, wherein $X^1$ represents methionine or is absent, $X^2$ represents glycine or is absent, and $X^3$ represents an amino acid residue (SEQ ID NO:9), said RNase A superfamily polypeptide being selectively toxic to a proliferating endothelial cell; and a pharmaceutically acceptable carrier.

In a further aspect, the invention provides a method of selectively inhibiting the growth of a proliferating endothelial cell by contacting said cell with an RNase A superfamily polypeptide comprising an N-terminus of the sequence: $X^1X^2SLX^3V$, wherein $X^1$ represents methionine or is absent, $X^2$ represents glycine or is absent and $X^3$ represents an amino acid residue (SEQ ID NO:9), said RNase A superfamily polypeptide being selectively toxic to a proliferating endothelial cell; and detecting the inhibition of the growth of said cell.

Preferably, the invention provides that a method of selectively inhibiting the growth of a proliferating endothelial cell that is a neoplastic cell. More preferably, the invention provides a method of selectively inhibiting the growth of a neoplastic cell that is Kaposi sarcoma cell.

In one aspect, the invention provides a method of treating a patient with proliferating endothelial cells by administering an effective amount of an RNase A superfamily polypeptide comprising an N-terminus of the sequence: $X^1X^2SLX^3V$, wherein $X^1$ represents methionine or is absent, $X^2$ represents glycine or is absent, and $X^3$ represents an amino acid residue (SEQ ID NO:9), said RNase A superfamily polypeptide being selectively toxic to a proliferating endothelial cell; and detecting the amelioration of Kaposi sarcoma in said patient.

In a further aspect, the invention provides a method of selectively treating a patient with proliferating endothelial cells where the RNase A superfamily polypeptide is in an aqueous solution comprising a unit dosage and pharmaceutically acceptable excipients. Preferably, the proliferating endothelial cells are Kaposi's sarcoma cells. More preferably, the proliferating endothelial cells are KS 1, KS 2, KS 3, KS 4, KS 5, KS 6, KS Y-1, and KS Y-3 cells.

The invention also provides a method of manufacturing a pharmaceutical composition comprising the step of combining the RNase A superfamily polypeptide with a pharmaceutically acceptable carrier.

BRIEF DESCRIPTION OF THE DRAWINGS

FIG. 1 shows a sequence alignment of some members of the RNase A superfamily: Frog lectin is from Rana catesbeiana (SEQ ID NO:18), onconase (SEQ ID NO:19), EDN (SEQ ID NO:6, ECP (human eosinophil cationic protein) (SEQ ID NO:20), ANG is bovine angiogenin (SEQ ID NO:21), seminal is bovine seminal RNase (SEQ ID NO:22), and RNase A is bovine pancreatic RNase A (SEQ ID NO:23). Amino acids conserved in all members are capitalized, and active site residues H12, K41, and H119 (RNase A numbering) are marked with an asterisk.

FIG. 7 is a graph of the % of protein synthesis in the absence of (−4)rhEDN versus the concentration of (−4)rhEDN. Open boxes, HBV immortalized HUVECs; semi-solid boxes, primary HUVECs; solid boxes, tumorigenic Ki-ras transformed HUVECs.

DESCRIPTION OF THE SPECIFIC EMBODIMENTS

Definitions

Figures 2, 3:
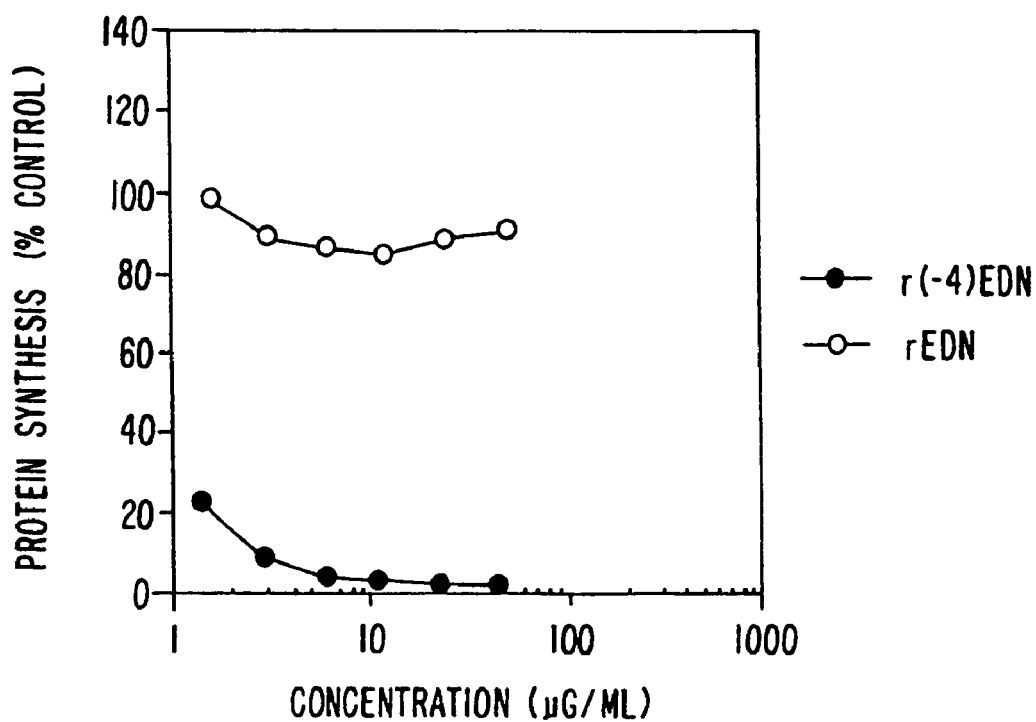
FIG. 2 shows the comparison of the sequences of the N-termini of rEDN (SEQ ID NO:24) and (−4)rEDN (SEQ ID NO:25).
FIG. 3 shows that protein synthesis in KS Y-1 cells is drastically decreased when (−4)rEDN is added to the cells, whereas rEDN does not have a significant impact on the growth of KS Y-1 cells.

Unless defined otherwise herein, all technical and scientific terms used herein have the same meaning as commonly understood by one of ordinary skill in the art to which this invention belongs. Singleton et al. (1994) Dictionary of Microbiology and Molecular Biology, second edition, John Wiley and Sons (New York), and Hale and Marham (1991) The Harper Collins Dictionary of Biology, Harper Perennial (New York), provide one of skill in the art with a general dictionary of many of the terms used in this invention. Although methods and materials similar or equivalent to those described herein can be used in the practice or testing of the present invention, the preferred methods and materials are described. For purposes of the current invention, the following terms are defined below.

Amino acids may be referred to herein by either their commonly known three letter symbols or by the one letter symbols recommended by the IUPAC-IUB Biochemical Nomenclature Commission. Nucleotides, likewise, may be referred to by their commonly accepted single letter codes.

"Homology" of one polypeptide sequence to another reference polypeptide sequence is defined by the percentage of identity between the two polypeptides. "Percentage of sequence identity" is determined by comparing two optimally aligned sequences over a comparison window, wherein the portion of the polypeptide sequence in the comparison window may comprise additions or deletions, such as gaps, as compared to the reference sequence (which does not comprise additions or deletions) for optimal alignment of the two sequences. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity.

"Conservatively modified variations" of a particular amino acid sequence refer to those variations in amino acid residues that maintain functionally identical polypeptide as compared to that before the variation. Furthermore, one of skill will recognize that individual substitutions, deletions or additions which alter, add or delete a single amino acid or a small percentage of amino acids in an encoded sequence are "conservatively modified variations" where the alterations result in the substitution of an amino acid with a chemically similar amino acid. Conservative substitution tables providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W.H. Freeman and Company.

"Proliferating cells" refer to cells that are growing and increasing in number by means of reproduction of similar forms, it also refers to cells that are reproducing new growth rapidly and repeatedly.

"Endothelial cells" refer to the layer of flat cells lining especially blood and lymphatic vessels and the heart.

"The RNase A superfamily", refers to a group of ribonucleases that are homologous to bovine pancreatic ribonuclease A in sequence, and are enzymes which are transferases or phophodiesterases that can catalyze the hydrolysis of ribonucleic acid. They exist in many different organisms such as mouse, hamster, pig, ox, human, deer, hippopotamus, etc. The RNase A superfamily polypeptides share a common characteristics in that they are homologous to bovine pancreatic RNase A. For general discussion on the RNase A superfamily, see Beintema, J. J. and Kleineidam, R. G., *Cell. Mol. Life Sci.* 54: 825–832 (1998), entitled: *"The Ribonuclease A Superfamily: general discussion."*, and Beintema, J. J., et al., *Prog. Biophys. Mol. Biol.,* 51: 165–192 (1988), entitled: *"Molecular Evolution of the Ribonuclease Superfamily."* Many of such members are known and include, but are not limited to, frog lectin from Rana catesbaiana (Titani et al., *Biochemistry* 26:2189 (1987)); onconase (Rosenberg et al., *Proc. Natl. Acad. Sci. USA* 86:4460 (1989)); eosinophil derived neurotoxin (EDN) (Rosenberg et al., supra); human eosinophil cationic protein (ECP) (Rosenberg et al., *J. Exp. Med.* 170:163 (1989)); angiogenin (ANG) (Fodstad et al., *Cancer Res.* 44:862 (1984)); bovine seminal RNase (Preuss et al., *Nuc. Acids. Res.* 18:1057 (1990)); and bovine pancreatic RNase (Beintema et al., *Prog. Biophys. Mol. Biol.* 51:165 (1988)), references for all such proteins incorporated by reference herein. Amino acid sequence alignment for such RNases is depicted in FIG. 1. One distinctive feature of the RNase A superfamily is the multiplicity of representatives in these investigated species, indicating that gene duplications frequently occur in the family, both in ancestral vertebrate lines and in recently evolved taxa (Beintema, J. J. and Kleineidam, supra).

"EDN" stands for eosinophil derived neurotoxin. "rEDN" stands for recombinant eosinophil derived neurotoxin. The nucleic acid sequence and amino acid sequence for rEDN are listed as SEQ ID NO: 5 and SEQ ID NO: 6, respectively.

"r(−4)EDN" stands for recombinant eosinophil derived neurotoxin with an added 4 amino acid sequence at its amino terminus. The nucleic acid sequence and amino acid sequence for r(−4)EDN are listed as SEQ ID NO: 1 and SEQ ID NO: 2, respectively.

"r(−5)EDN" stands for recombinant eosinophil derived neurotoxin with an added 5 amino acid sequence at its amino terminus. The nucleic acid sequence and amino acid sequence for r(−5)EDN are listed as SEQ ID NO: 3 and SEQ ID NO: 4, respectively.

A modified RNase A superfamily polypeptide is said to be "selectively toxic" to a cell line when the growth of an endothelial cell line such as the KS Y-1 is inhibited by such a RNase A superfamily polypeptide treatment if, when assayed by means such as radioisotope incorporation into the cells, the treated cells proliferate at a rate that is less than about 80% of the proliferation rate of untreated control cells, and preferably less than about 70% of the untreated cell proliferation rate. More preferably, the growth rate is inhibited by at least 50%. If growth is assayed by a means such as plating in methylcellulose, the modified RNase A superfamily polypeptide is said to be "selectively toxic" to the cell line if the treated cells give rise to less than about 80% of the number of colonies that grow from a like number of untreated cells. Preferably, the number of colonies from treated cells is less than about 70% of the number from untreated cells. More preferably, the number of colonies is decreased by at least 50%.

The terms "neoplasia" or "neoplastic" are intended to describe a cell growing and/or dividing at a rate beyond the normal limitations of growth for that cell type.

The term "effective amount" means a dosage sufficient to produce a desired result. The desired result can be subjective or objective improvement in the recipient of the dosage, a decrease in tumor size, a decrease in the rate of growth of cancer cells, or a decrease in metastasis.

The term "treating a subject or a patient" means generally a treatment that causes any improvement in a subject or a patient having a cancer wherein the improvement can be ascribed to treatment with the modified RNase A superfamily polypeptide. The improvement can be either subjective or objective. For example, in the case of a patient, the patient may note improved vigor or vitality or decreased pain as subjective symptoms of improvement or response to therapy. Alternatively, the clinician may notice a decrease in tumor size or tumor burden based on physical exam, laboratory parameters, tumor markers, or radiographic findings.

The term "amelioration" or "ameliorate" refers to any indicia of success in the treatment of a pathology or condition, including any objective or subjective parameter such as abatement, remission or diminishing of symptoms or an improvement in a patient's physical well-being. The amelioration can be evaluated by any accepted method of measuring whether growth of the cancer cells has been slowed or diminished. This includes direct observation and indirect evaluation such as subjective symptoms or objective signs.

Introduction

This invention provides RNase A superfamily polypeptides with modified amino terminal which can be used to selectively kill target Kaposi's sarcoma cells. In certain embodiments of the invention, the amino terminal modification consists of an addition of 4 amino acid sequence consisting of the SLHV sequence at position −4 to −1 to the EDN protein. The amino terminal addition is capable of directing the claimed RNase A superfamily polypeptides to proliferating endothelial cells, such as Kaposi's sarcoma cells, and selectively killing these cells.

Modified RNase A Superfamily Polypeptides

The present invention provides a modified RNase A superfamily polypeptide which is a member of the RNase A superfamily. The RNase A superfamily can include ribonucleases from a variety of sources. For example, they can be originated from human, bovine, and frogs. Some examples of the RNase A superfamily are frog lectin, Onconase, eosinophil derived neurotoxin, human eosinophil cationic protein, bovine angiogenin, bovine seminal RNase, and bovine pancreatic RNase A. Members of the RNase A superfamily have molecular weight ranges from about 12 kDa–16 kDa. See Youle et al., *Critical Rev. in Therapeutic Drug Carrier Systems*, 10(1): 1–28, 1993. These members of the RNase A superfamily tend to be homologous to each other in sequence. They share conservative amino acids and active site residues for their RNase activities. The percentage of identity among the RNase A superfamily members varies from 22% to 81%. Functionally, they have been shown to be anti-tumor agents. See Youle, et al, supra.

In one aspect of the invention, eosinophil-derived neurotoxin (EDN) molecule is modified at the amino terminal so that it selectively kills the growth of KS Y-1 cells.

On the one hand, one can produce modified RNase A superfamily polypeptides that are useful in the present invention by chemical or enzymatic synthesis. Solid phase synthesis in which the C-terminal amino acid of the sequence is attached to an insoluble support followed by sequential addition of the remaining amino acids in the sequence is the preferred method for the chemical synthesis of the modified RNase A superfamily polypeptides as claimed in this invention. Techniques for solid phase chemical synthesis of proteins are described, for example, in Barany and Merrifield, *Solid-Phase Peptide Synthesis*, pp. 3–284 in *The Peptides: Analysis, Synthesis, Biology*. Vol. 2: Special Methods in Peptide Synthesis, Part A, Merrifield, *J. Amer. Chem. Soc.* 85: 2149–2156 (1963), and Stewart et al., *Solid Phase Peptide Synthesis*, $2^{nd}$ ed. Pierce Chem. Co, Rockford, Ill. (1984). This reference is incorporated herein by reference.

A preferred method for producing the RNase A superfamily polypeptides of the invention involves recombinant expression. For this purpose, natural or synthetic nucleic acids that code for the claimed RNase A superfamily polypeptides will typically be operably linked to a promoter to form an expression cassette. The sequences of the RNase A superfamily members, such as EDN, is known in the art. Rosenberg, H. F. and Dyer, K. D., (1995) *J. Biol. Chem.*, 37: 21539–21544. Therefore, one of skill can readily identify and clone the cDNAs that code for these. Alternatively, one can synthesize the desired coding regions chemically.

To produce the RNase A superfamily polypeptides claimed in this invention using recombinant DNA technology, one introduces an expression cassette that codes for the RNase A superfamily polypeptide into an appropriate host cell. Suitable host cells include yeast, filamentous fungi, insects (especially employing baculoviral vectors), and mammalian cells, as well as bacterial systems.

Mammalian or insect cell expression systems are preferred, since protein folding, transport and processing (including glycosylation) closely approximate that which occurs in the human, see, e.g., E. Winnacker, *From Genes to Clones*, VCH Publishers, New York (1987), which is incorporated herein by reference. For examples of suitable expression systems for the RNase A superfamily polypeptides useful in the present invention, see, e.g., Corless et al. (1987) *J. Biol. Chem.* 262: 14187–14203; Lustbader et al. (1987) *J. Biol. Chem.* 262: 14204–14212; Huang et al. (1993) *Mol Cell. Endocrinol.* 90: 211–218; Reddy et al., (1985) *Proc. Natl. Acad. Sci. USA* 8: 3644–3648; all of which are incorporated herein by reference.

Once expressed, one can purify the RNase A superfamily polypeptides from lysed cells or, preferably, from culture medium into which the RNase A superfamily polypeptides are secreted. Standard procedures of the art are suitable, including ammonium sulfate precipitation, affinity columns, column chromatography, gel electrophoresis and the like (see, generally, R. Scopes, *Protein Purification*, Springer-Verlag, NY (1982), which is incorporated herein by reference). Substantially pure RNase A superfamily polypeptides of at least about 90 to 95% homogeneity are preferred, and those of 98 to 99% or greater homogeneity most preferred, for pharmaceutical uses.

Another method of purifying the RNase A superfamily polypeptides as claimed in this invention is by Sephadex G-100 Column Chromatography. To start the purification process, samples containing the polypeptides are dissolved in solvent, and then separated into tubes on a Sephadex G-100 column. The tubes are pooled for different fractions, and each fraction is lyophilized. The process of fractionating and lyophilizing is repeated. Polypeptides content is monitored by measuring the absorbance at 229 nm. Peaks of polypeptides are collected, lyophilized, and dissolved in water or saline for further analysis. See Sakakibara, et al., *Chem. Pharm. Bull.* 39(1): 146–149 (1991).

Yet another method of purifying the claimed RNase A superfamily polypeptides is by reverse-phase HPLC. Methods such as reverse-phase HPLC is well known in the art.

As an example, the RNase A superfamily polypeptides claimed in this invention can be manufactured using methods for expression and purification of modified EDN that are taught in Newton, et al., *J. Biol. Chem.* 269: 26739–26745 (1994). This reference is herein incorporated by reference in order to produce the claimed RNase A superfamily polypeptides in this invention.

The present invention includes those RNase A superfamily polypeptides with conservative amino acid substitutions, additions, deletions, and other changes which do not affect its RNase activity and its toxicity in killing their target cells such as KS Y-1 cells. It is recognized that amino acid residues in the RNase A superfamily polypeptides may be replaced by other amino acid residues with similar chemical properties (e.g., charge or hydrophobicity). Because the substituted amino acids have similar properties, the substitutions do not change the functional properties of the polypeptides. As discussed above, it is apparent that the RNase A superfamily polypeptides have varies amino acids that won't change their functions significantly. The following six groups each contain amino acids that are conservative substitutions for one another:
 1) Alanine (A), Serine (S), Threonine (T);
 2) Aspartic acid (D), Glutamic acid (E);
 3) Asparagine (N), Glutamine (Q);
 4) Arginine (R), Lysine (K);
 5) Isoleucine (I), Leucine (L), Methionine (M), Valine (V); and
 6) Phenylalanine (F), Tyrosine (Y), Tryptophan (W).

The present invention teaches that, regardless of the variations of the amino acid residues in the RNase A superfamily polypeptides, their active biological activities are maintained. The invention teaches that the RNase activity of the claimed modified RNase A superfamily polypeptides can be tested using methods well known in the art. In these testing experiments, transfer RNA serves as a substrate to be digested by RNases, and human serum albumin is used to buffer the reaction. All assays are performed in the linear range of the RNase in general. Absorbance readings of control groups are subtracted from assays containing the RNase A superfamily polypeptides to be tested. See Newton, et al., *J. Biol. Chem.* 269: 26739–26745 (1994).

Adding the Amino Terminal Sequence to the RNase A Superfamily Polypeptides

The modified RNase A superfamily polypeptides can be manufactured by adding to the N terminus of mature EDN protein a short amino acid sequence in the length of 4–6 amino acids. The N-terminus has the sequence: $X^1X^2SLX^3V$, wherein $X^1$ represents methionine or is absent, $X^2$ represents glycine or is absent, and $X^3$ represents an amino acid residue (SEQ ID NO:9). For example, the N terminus can have the sequence of MGSLXV (SEQ ID NO:12), MSLXV (SEQ ID NO:13), GSLXV (SEQ ID NO:14), or SLXV (SEQ ID NO:15), where X is an amino acid.

To produce the modified EDN protein, oligonucleotides can be synthesized to modify the DNA encoding EDN, and overlap PCR extension reaction is used to create a recombinant version of EDN with an extended amino terminal. PCR overlap extension technique is known to one of skill in the art. Horton et al., (1990) *Biotechniques,* 8:528–535.

In general, nucleic acids encoding the claimed RNase A superfamily polypeptides can be made using standard recombinant or synthetic techniques. Due to the degeneracy of the genetic code, more than one nucleic acid sequence may code for the same amino terminal sequence of the modified RNase A superfamily polypeptide. Given the nucleic acids of the present invention, one of skill can construct a variety of clones containing functionally equivalent nucleic acids, such as nucleic acids which encode the same polypeptide. Cloning methodologies to accomplish these ends, and sequencing methods to verify the sequence of nucleic acids are well known in the art. Examples of appropriate cloning and sequencing techniques, and instructions sufficient to direct persons of skill through many cloning exercises are found in Berger and Kimmel, *Guide to Molecular Cloning Techniques, Methods in Enzymology*, volume 152 Academic Press, Inc., San Diego, Calif. (Berger); Sambrook et al. (1989) *Molecular Cloning—A Laboratory Manual* (2nd ed.) Vol. 1–3; and *Current Protocols in Molecular Biology*, F. M. Ausubel et al., eds., Current Protocols, a joint venture between Greene Publishing Associates, Inc. and John Wiley & Sons, Inc., (1994 Supplement) (Ausubel). Product information from manufacturers of biological reagents and experimental equipment also provide information useful in known biological methods. Such manufacturers include the SIGMA chemical company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), Invitrogen, San Diego, Calif., and Applied Biosystems (Foster City, Calif.), as well as many other commercial sources known to one of skill.

In vitro amplification techniques suitable for amplifying sequences for use in generating nucleic acid fragments for subsequent subcloning are known. Examples of techniques sufficient to direct persons of skill through such in vitro amplification methods, including the polymerase chain reaction (PCR), the ligase chain reaction (LCR), Qβ-replicase amplification and other RNA polymerase mediated techniques (e.g., NASBA) are found in Sambrook et al. (1989) *Molecular Cloning—A Laboratory Manual*(2nd Ed) Vol. 1–3; and as well as Mullis et al., (1987) U.S. Pat. No. 4,683,202; PCR Protocols A Guide to Methods and Applications (Innis et al. eds) Academic Press Inc. San Diego, Calif. (1990) (Innis); Arnheim & Levinson (Oct. 1, 1990) C&EN 36–47; *The Journal Of NIH Research* (1991) 3, 81–94; (Kwoh et al. (1989) *Proc. Natl. Acad. Sci. USA* 86, 1173; Guatelli et al. (1990) *Proc. Natl. Acad. Sci. USA* 87, 1874; Lomell et al. (1989) *J. Clin. Chem* 35, 1826; Landegren et al., (1988) *Science* 241, 1077–1080; Van Brunt (1990) *Biotechnology* 8, 291–294; Wu and Wallace, (1989) *Gene* 4, 560; Barringer et al. (1990) *Gene* 89, 117, and Sooknanan and Malek (1995) *Biotechnology* 13: 563–564. Improved methods of cloning in vitro amplified nucleic acids are described in Wallace et al., U.S. Pat. No. 5,426,039.

Oligonucleotides for use as primers in nucleic acid amplification methods are typically synthesized chemically according to the solid phase phosphoramidite triester method described by Beaucage and Caruthers (1981), *Tetrahedron Letts.*, 22(20):1859–1862, e.g., using an automated synthesizer, e.g., as described in Needham-VanDevanter et al. (1984) *Nucleic Acids Res.*, 12:6159–6168. Oligonucleotides can also be custom made and ordered from a variety of commercial sources known to persons of skill. Purification of oligonucleotides, where necessary, is typically performed by either native acrylamide gel electrophoresis or by anion-exchange HPLC as described in Pearson and Regnier (1983) *J. Chrom.* 255:137–149. The sequence of the synthetic oligonucleotides can be verified using the chemical degradation method of Maxam and Gilbert (1980) in Grossman and Moldave (eds.) Academic Press, New York, *Methods in Enzymology* 65:499–560.

One of skill will recognize many ways of generating desired alterations in a given nucleic acid sequence in order to produce desired modification to the amino terminal of the RNase A superfamily polypeptides. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, Giliman and Smith (1979) *Gene* 8:81–97; Roberts et al. (1987) *Nature* 328:731–734 and Sambrook et al. (1989) *Molecular Cloning—A Laboratory Manual* (2nd Ed) Vol. 1–3; Innis, Ausubel, Berger, Needham VanDevanter and Mullis (all supra).

Polypeptides of the invention can be synthetically prepared in a wide variety of well-known ways. Polypeptides of relatively short size are typically synthesized in solution or on a solid support in accordance with conventional techniques. See, e.g., Merrifield (1963) *J. Am. Chem. Soc.* 85:2149–2154. Various automatic synthesizers and sequencers are commercially available and can be used in accordance with known protocols. See, e.g., Stewart and Young (1984) *Solid Phase Peptide Synthesis*, 2d. ed., Pierce Chemical Co. Polypeptides are also produced by recombinant expression of a nucleic acid encoding the polypeptide followed by purification using standard techniques.

The present invention teaches how to make the desired modification to the amino terminal of EDN protein as shown in Example 2. 5' oligonucleotides can be made so as to incorporate the nucleic acid sequence that encodes the desired amino acid sequence to the amino terminus of the EDN protein. Various primers can be synthesized according to standard protocol in the art in order to obtain the desired sequence. Similarly, 3' oligonucleotide sequence can be synthesized. After the synthesis of the oligonucleotides, standard PCR procedures are performed, for example, following those PCR protocols using Gene Clean II of Bio101, Inc., of La Jolla, Calif.

The present invention includes methods of confirming that correct nucleic acid sequence encoding the desired amino acid addition has been incorporated into the EDN protein, the end product of the modified EDN is sequenced using double-stranded DNA templates according to the Sequenase II protocols of United States Biochemical Corp.

Another method of confirming the amino terminal sequence of the modified RNase A superfamily polypeptide is analyzing the polypeptide on an automated Applied Biosystems model 477A protein sequencer equipped with an online phenylthiohydantoin (PTH) analyzer. See Sakakibara, et al., *Chem. Pharm. Bull.* 39(1): 146–149 (1991).

The modified EDN proteins as claimed in this invention include those EDN with an added 4-amino acid sequence extension to the amino terminal of EDN. The modified EDN can also have a six-amino acid fragment added to its amino terminal.

Phage Display of RNase A Superfamily Peptides.

The modified RNase A superfamily polypeptides can be displayed on the surface of a phage as a fusion protein with a capsid protein. DNA fragments containing a modified RNase A superfamily polypeptide can be subcloned into a phage construct that will permit the expression of the phage displayed fusion protein. Phage display technology is based on a report published in 1985 describing the in-frame insertion of a DNA fragment encoding a section of the restriction endonuclease EcoRI into the gene of a minor capsid protein (g3p) of the filamentous bacteriophage fd. Smith, G. P. (1985) *Science,* 228: 1315–1317. The foreign protein was displayed on the surface of the fusion phage and was immunologically accessible.

The filamentous bacteriophage (such as f1 phage, fd phage, and M13 phage) contains circular single-strand DNA encoding 10 proteins from a genome of approximately 6500 nucleotides in length. See Model and Russell, (1988), *The Bacteriophages, Vol* 2., R. Calendar (Ed.), Plenum Press, New York. The infectious cycle of filamentous bacteriophage begins with the attachment of the phage via g3p to the tip of the F-pilus of the host bacterial cell. The phage DNA then enters the cell by an unknown mechanism. Upon entry to the cytoplasm, the single stranded DNA is converted into a double-stranded replicative form by the action of host-cell proteins. The replicative DNA serves as a template for the synthesis of viral proteins, and further single stranded (+) DNA for incorporation into progeny particles.

An important feature of filamentous bacteriophage is their ability to package longer genomes than the wild-type DNA. Fusion phages have been generated with insertions into either the minor capsid protein g3p for large insertions, or the major capsid protein g8p for short peptide insertions. Smith, 1985. In these fusion phages, the DNA encoding the insert protein is packaged as an integral part of the phage genome, while the chimeric protein product is expressed on the surface of the phage particle, allowing the simultaneous selection of a gene and its protein.

Phage display using a filamentous bacteriophage system can be classified as Types 3, 3+3, 33, 8, 8+8, or 88 depending on the use of g3p or g8p as the fusion partner, the number of fusion products, and the vectors employed. Smith, 1985. In the type 3 system, the foreign DNA is inserted in frame with the gene 3 of the filamentous bacteriophage. This enables the display of a foreign polypeptide fused with each copy of the g3p protein on the surface of the recombinant phage surface. In Type 33 display, the wild-type g3p protein and the foreign product-g3p fusion are encoded in a single recombinant phage genome by using a phage vector. In Type 3+3 display, there are also two types of g3p protein (the wild-type and foreign protein-g3p fusion) on the surface of the recombinant phage. But the foreign protein-g3p fusion is encoded by a phagemid (a plasmid containing phage origins of replication and packaging signal) while the wild-type g3p protein and all other phage proteins are encoded by a helper phage. Superinfection of the phagemid-harboring bacterial cells with helper phage yields viral particles containing phagemid single-strand DNA as well as the helper phage DNA. Types 8, 88, and 8+8 of display are the g8p counterparts to the Types 3, 33, and 3+3 system. The choice of a particular system depends on the size of the insert in the fusion protein and the number of fusion proteins required to be displayed on each phage particle. The major limitation in the use of g3p fusions to display peptides or proteins is the number of fusion proteins that can be displayed on each particle—a maximum of five fusion protein copies can be displayed if the native g3p protein is not required to ensure infectivity. On the other hand, insertion into the major capsid protein g8p has a size limitation—only 5–6 extra amino acids are tolerated if present on all of g8p subunits on the capsid. Greenwood et al. (1991) *J. Mol. Biol.*, 220: 821–827. Large peptides can be displayed on hybrid virions in Types 8+8 and 88 display system in which wild-type and chimeric g8p molecules are interspersed. Smith, 1985.

The phage display technology can be used to display enzymes. In fact, the first foreign protein displayed on filamentous bacteriophage was the enzyme EcoRI that was inserted into the filamentous phage minor coat protein g3p. Smith, (1985). The resulting fusion phage retained infectivity in spite of the foreign protein—g3p fusion being displayed on the phage surface. The displayed EcoRI endonuclease was recognized by an EcoRI specific antibody. Many other enzymes have also been displayed using phage display system, including: Staphylococcal nuclease, (Light and Lerner, (1995) *Bioorg. Med. Chem.*, 3: 955–967, Pedersen et al., (1998) *Proc. Natl. Acad. Sci., U.S.A.* 95: 10523–10528), trypsin (Corey et al., (1993) *Gene*, 128: 129–134) and beta-lactamase (Rudgers and Palzkill, (1999) *J. Biol. Chem.* 274: 6963–6971, Legendre et al., (1999) *Nat. Biotechnol.*, 17, 67–72).

The phage display technology can be used to express a amino-terminal modified RNAse A superfamily polypeptide on the surface of the phage. For example, an EDN molecule that has been modified on the N-terminal with the peptide SLHV can be expressed on phage using the phage display technology. A DNA fragment containing the modified RNase A superfamily polypeptide member can be ligated into a restricted phage vector that can direct the expression of the modified RNase-capsid protein fusion protein. The resulting recombinant phage expressing the RNase-capsid protein fusion can be then tested for the retention of RNAS activity and for its ability to inhibit the growth of cells.

Testing for Efficacy Against Proliferating Endothelial Cells

The present invention provides methods of selectively inhibiting the growth of proliferating endothelial cells. There are assays and experiments one can perform in order to determine that the modified RNase A superfamily polypeptides are indeed active molecules in killing their target cells, such as Kaposi's sarcoma cells. The modified RNase A superfamily polypeptides of the present invention are also effective in inhibiting the growth of endothelial cells of other types of cancers. For example, the modified RNase A superfamily polypeptides are also antiangiogenic and are useful for treating cancers that involve angiogenesis, regardless of the cell origins (i.e., those cancers that are of non-endothelial origins). These cancers can include thoracic aortic angiosarcoma, epithelioid hemangioendothelioma, haemangioblastoma, and lung cancer etc.

One of skill in the art can test the efficacy of the claimed RNase A superfamily polypeptides against a particular tumor type, either in vitro or in vivo. For in vitro tests, cells derived from the tumor are grown in the presence or absence of the RNase A superfamily polypeptide and the effect of the RNase A superfamily polypeptide is determined. One commonly utilized assay for tumor cell growth is the methylcellulose assay (Lunardi-Iskandar et al. (1985) Clin. Exp. Immunol. 60: 285–293). Generally, the cells are plated in medium containing methylcellulose, which prevents nontumor cells from undergoing mitosis and forming colonies. The RNase A superfamily polypeptides of the invention prevent tumor cells from forming as many colonies as untreated cells. Another means for measuring the inhibitory effect of the claimed RNase A superfamily polypeptides is by measuring the rate of incorporation of radiolabelled metabolites such as tritiated thymidine.

The claimed RNase A superfamily polypeptides are effective in killing non-neoplastic cell lines. For example, the claimed polypeptides are useful in inhibiting the growth of Human Umbilical Vein Endothelial Cells (HUVEC). These cells can be purchased from Clonetics Corporation (San Diego, Calif.) under the Catalogue Number 2619.

The polypeptides of the present invention are cytotoxic against the Lewis lung cell line, which is a model for angiogenesis. The Lewis lung cell line is a mouse lung carcinoma cell line. They are deposited with ATCC, under the Accession No. CRL-1642.

The present invention also relates to a method of using the claimed modified EDN to selectively kill Kaposi's sarcoma cells. A preferred embodiment of target cells for the RNase A superfamily polypeptides is Kaposi's sarcoma cells: KS Y-1 cells. These cells are known in the art, as described in Lunardi-Iskandar, et al., *J. N. Cancer Inst.* 87: 974–981 (1995). The cells are also taught in U.S. Pat. No. 5,569,602. They are deposited with ATCC, under the Accession No. 14488.

Other embodiments of the invention can include selectively inhibiting the growth of other Kaposi's sarcoma cell strains such as KS 1, KS 2, KS 3, KS 4, KS 5, and KS 6. They are described in Nakamura et al., *Science* 242: 426–430, 1988, and Salahuddin et al., *Science* 242: 430–433, 1988. The RNase A superfamily polypeptides can also be used to inhibit the growth of KS Y-3 cells, which are described in Lunardi-Iskandar, *J. Nat'l Cancer Inst.,* 87(13): 974–981, 1995.

In addition to testing a RNase A superfamily polypeptide for efficacy against a particular tumor cell type in vitro, the clinician can test the RNase A superfamily polypeptide in vivo. For in vivo tests, cells derived from the tumor type are injected into laboratory animals such as immunodeficient mice. Typically, either the laboratory animals or the cells have been pre-treated with the claimed RNase A superfamily polypeptide. The animals are then monitored to determine whether tumors arise at the site of injection, or elsewhere in the animal.

One method for carrying out these in vivo tests is as follows. The tumor cells to be tested are grown for 48 hours in the RPMI culture medium as disclosed in Example 4 of this invention, plus 10% fetal calf serum in the presence of 100 USP units/ml RNase A superfamily polypeptide per ml. As a control, tumor cells are grown in the absence of the RNase A superfamily polypeptide. Approximately $5 \times 10^6$ cells are then subcutaneously injected into SCID or nude mice (Beige, BALB/c, Swiss, or NCr (see, e.g., Croyba et al. (1993) *Laboratory Animal Science* 43: 120–122)). Alternatively, the efficacy of a claimed RNase A superfamily polypeptide against a tumor cell type can be tested by inoculating a mouse with the RNase A superfamily polypeptide before challenge with the tumor cells, rather than pretreating the cells. For example, mice can be injected with 10–100 USP units of the modified RNase A superfamily polypeptide daily for 5–7 days before challenge with the tumor cells.

Laboratory animals that are either treated with a RNase A superfamily polypeptide as claimed in this invention prior to tumor cell inoculation, or inoculated with tumor cells that have been grown in the presence of the RNase A superfamily polypeptide, typically will not develop tumors. For example, in the absence of the RNase A superfamily polypeptide pretreatment, Kaposi's sarcoma cells will typically induce a strong angiogenic reaction at the site of inoculation within seven days. Tumors will usually develop and persist for an extended period of time. These tumors can occur at the site of injection and also as metastases in one or more of the lung, spleen, skin, or pancreas. Typically, tumors induced by the KS cell lines will metastasize. Mice that are injected with Kaposi's sarcoma cells that have been pretreated with the claimed RNase A superfamily polypeptide, or mice that have been pre-inoculated with the RNase A superfamily polypeptide before challenge with the Kaposi's sarcoma cells, do not develop tumors within two months post-challenge.

Formulation of Modified the RNase A Superfamily Polypeptides

Topical Formulations

The present invention provides methods of treating patients with Kaposi's sarcoma with a pharmaceutical composition containing the modified RNase A superfamily polypeptides by applying the claimed composition to the patients in a variety of ways, such as topically, and parenterally or intralesionally. Oral administration is used in appropriate circumstances apparent to the practitioner. Preferably, the compositions are administered in unit dosage forms suitable for single administration of precise dosage amounts.

To prepare a topical formulation, a therapeutically effective concentration of the polypeptide is placed in a dermatological vehicle as is known in the art. The amount of the polypeptide to be administered and its concentration in the topical formulations depend upon the vehicle selected, the clinical condition of the patient, the side effects and the stability of the polypeptide in the formulation. Thus, the physician employs the appropriate preparation containing the appropriate concentration of the polypeptide and selects the amount of formulation administered, depending upon clinical experience with the patient in question or with similar patients.

The concentration of the polypeptide for topical formulations is in the range of about 1 mg/ml to about 100 mg/ml. Typically, the concentration of the polypeptide for topical formulations is in the range of about 2.5 mg/ml to about 25 mg/ml. Solid dispersions of the polypeptide as well as solubilized preparations can be used. Thus, the precise concentration is subject to modest experimental manipulation in order to optimize the therapeutic response. About 2,500 mg of polypeptide per 100 grams of vehicle is useful in the treatment of skin lesions to provide a 2.5% weight/weight (w/w) formulation. Suitable vehicles include oil-in-water or water-in-oil emulsions using Aloe, mineral oils, petrolatum and the like as well as gels such as hydrogel.

Alternative topical formulations include shampoo preparations, oral paste, and mouth wash preparations. ORABASE (Registered TM) can be used as the base oral paste to which the polypeptide is added. Concentrations of polypeptide are typically as stated above for topical formulations.

The polypeptide is optionally administered topically by the use of a transdermal therapeutic system (see Barry, *Dermatological Formulations*, (1983) p. 181 and the literature cited therein). While such topical delivery systems have been designed largely for transdermal administration of low molecular weight drugs, by definition they are capable of percutaneous delivery. They may be readily adapted to administration of the polypeptides of the invention by appropriate selection of the rate-controlling microporous membrane.

The polypeptide is alternatively administered by aerosol. This is accomplished by preparing an aqueous aerosol, liposomal preparation or solid particles containing the polypeptide. A nonaqueous (e.g., fluorocarbon propellant) suspension could be used. Sonic nebulizers are preferred because they minimize exposing the polypeptide to shear, which can result in degradation of the polypeptide.

Ordinarily, an aqueous aerosol is made by formulating an aqueous solution or suspension of the polypeptide together with conventional pharmaceutically acceptable carriers and stabilizers. The carriers and stabilizers vary with the requirements of the particular polypeptide, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Oral Formulation

For oral administration, either solid or fluid unit dosage forms can be prepared. For preparing solid compositions such as tablets, thiazolidine derivatives are mixed into formulations with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the thiazolidine compound with an inert pharmaceutical diluent and filling the mixture into a hard gelatin capsule of appropriate size. Soft gelatin capsules are prepared by machine encapsulation of a slurry of the thiazolidine compound with an acceptable vegetable oil, light liquid petrolatum or other inert oil.

Fluid unit dosage forms for oral administration such as syrups, elixirs and suspensions can be prepared. The water-soluble forms can be dissolved in an aqueous vehicle together with sugar, aromatic flavoring agents and preservatives to form a syrup. An elixir is prepared by using a hydroalcoholic (e.g., ethanol) vehicle with suitable sweeteners such as sugar and saccharin, together with an aromatic flavoring agent. Suspensions can be prepared with an aqueous vehicle with the aid of a suspending agent such as acacia, tragacanth, methylcellulose and the like.

Intralesional Formulations

Appropriate formulations for parenteral and intralesional use are apparent to the practitioner of ordinary skill. Usually, the polypeptide is prepared in an aqueous solution in a concentration of from about 1 to about 100 mg/ml. More typically, the concentration is from about 10 to about 20 mg/ml. The formulation, which is sterile, is suitable for various parenteral routes including intra-dermal, intra-articular, intra-muscular, intravascular, and subcutaneous. Preferably, intralesional injection is used.

Carriers

In addition to the polypeptide, the compositions may include, depending on the formulation desired, pharmaceutically-acceptable, non-toxic carriers or diluents, which include vehicles commonly used to form pharmaceutical compositions for animal or human administration. The diluent is selected so as not to unduly affect the biological activity of the combination. Examples of such diluents which are especially useful for injectable formulations are water, the various saline solutions, Ringer's solution, dextrose solution, and Hank's solution. In addition, the pharmaceutical composition or formulation may include additives such as other carriers; adjuvants; or nontoxic, nontherapeutic, nonimmunogenic stabilizers and the like.

Furthermore, excipients can be included in the formulation. Examples include co-solvents, surfactants, oils, humectants, emollients, preservatives, stabilizers and antioxidants. Any pharmacologically acceptable buffer may be used, e.g., Tris or phosphate buffers. Effective amounts of diluents, additives and excipients are those amounts which are effective to obtain a pharmaceutically acceptable formulation in terms of solubility, biological activity, etc.

Different carries are appropriate for the pharmaceutical composition of the RNase A superfamily polypeptides, depending upon the mode of administration. The pharmaceutical compositions of this invention are particularly useful for parenteral administration, such as intralesional injection into the tumor in the skin. The compositions for administration will commonly comprise a solution of the RNase A superfamily polypeptide dissolved in a pharmaceutically acceptable carrier, preferably an aqueous carrier. A variety of aqueous carriers can be used, e.g., water, buffered water, 0.4% saline, 0.3% glycine, hyaluronic acid and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of therapeutic molecule in these formulations can vary widely, and will be selected primarily based on fluid volumes, viscosity, body weight and the like in accordance with the particular mode of administration selected and the patient's needs.

Dosage Form

The term "unit dosage form" refers to physically discrete units suitable as unitary dosages for human subjects and animals, each unit containing a predetermined quantity of active material calculated to produce the desired pharmaceutical effect in association with the required pharmaceutical diluent, carrier or vehicle. The specifications for the unit dosage forms of this invention are dictated by and dependent on (a) the unique characteristics of the active material and the particular effect to be achieved and (b) the limitations inherent in the art of compounding such an active material for use in humans and animals.

Examples of unit dosage forms are tablets, capsules, pills, powder packets, wafers, suppositories, granules, cachets, teaspoonfuls, tablespoonfuls, dropperfuls, ampoules, vials, aerosols with metered discharges, segregated multiples of any of the foregoing, and other forms as herein described.

Thus, a composition of the invention includes a polypeptide which may be formulated with conventional, pharmaceutically acceptable vehicles for topical, oral or parenteral administration. Formulations may also include small amounts of adjuvants such as buffers and preservatives to maintain isotonicity, physiological and pH stability. Means of preparation, formulation and administration are known to those of skill. A typical pharmaceutical composition for intravenous infusion could be made up to contain 250 ml of sterile Ringer's solution, and 3000–5000 USP units of RNase A superfamily polypeptide. Actual methods for preparing parenterally administrable polypeptides will be known or apparent to those skilled in the art and are described in more detail in for example, Remington's Pharmaceutical Science, 17th ed., Mack Publishing Company, Easton, Pa. (1985), which is incorporated herein by reference.

For solid form of the RNase A superfamily polypeptide pharmaceutical compositions of the invention, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more anti-cancer RNase A superfamily polypeptides, more preferably at a concentration of 25%–75%.

Administration of the Claimed RNase A Superfamily Polypeptides

Pharmaceutical compositions containing the RNase A superfamily polypeptides described herein are administered to an individual having cancer such as Kaposi's sarcoma. In therapeutic applications, compositions are administered to a human patient in an amount sufficient to cause regression of the tumor, or at least partially arrest the tumorigenesis and metastasis. An amount adequate to accomplish this is defined as a "therapeutically effective dose." Amounts effective for this use will depend on, e.g., the nature of the RNase A superfamily polypeptide (specific activity, etc.), the manner of administration, the stage and severity of the cancer, the weight and general state of health of the patient, and the judgment of the prescribing physician. Typically, doses will range from about 3000 to about 5000 USP units of RNase A superfamily polypeptide per day per 70 kg patient. If a cancer has metastasized a larger dose can be employed. Generally, the dose will be repeated daily until the tumors are gone. Typically, a minimum of one to two weeks of treatment is required. One with ordinary skill in the art would know how to perform clinical studies involving reducing the Kaposi's sarcoma symptom of AIDS patients, for example, as disclosed in P. S. Gill et al., *J. Nat'l Cancer Inst.* 89: 1797–1802, 1997.

Single or multiple administrations of the RNase A superfamily polypeptide compositions can be carried out with dose levels and pattern being selected by the treating physician. In any event, the pharmaceutical formulations should provide a quantity of the RNase A superfamily polypeptide sufficient to effectively treat the patient. Administration should begin at the first indication of undesirable cellular proliferation or shortly after diagnosis, and continue until symptoms are substantially abated and for a period thereafter. In well established cases of cancer, loading doses followed by maintenance doses will be required.

Patients who are injected with the RNase A pharmaceutical composition are monitored for their progress on reduction of cancer growth. In the case of Kaposi's sarcoma cancer patients, the method of injection is preferably intralesional, or subcutaneous injections. The course of therapy is at least 14 days, and injection is performed daily or three times a week. A complete response in Kaposi's sarcoma patients is defined as complete flattening of all lesions, clinical evidence of complete resolution of all disease, and the absence of detectable disease in any lesions that may have had residual pigments, as confirmed by biopsy. Such response should last for at least four weeks without the development of any new KS lesions. A partial response is defined as fulfilling at least one of the following criteria: a decrease of at least 50% in the number of lesions, a complete flattening of previously nodular lesions by 50% or higher, or a 50% or higher decrease in the sum of the perpendicular diameter of the indicator lesions. Again, the response must last for at least four weeks or longer with development of new KS lesions.

EXAMPLES

The following examples are provided by way of illustration only, and not by way of limitation. Those of skill in the art will readily recognize a variety of noncritical parameters which could be changed or modified to yield essentially similar results.

1. Construction of a Synthetic Gene Encoding rEDN

A synthetic gene encoding EDN (rEDN) was designed using the *E. coli* preferred codon bias (Grantham, R. et al., Nucleic Acids Res. 9: 43–74 (1981)). The gene was constructed from 10 pairs of complementary oligonucleotides. Oligonucleotides were synthesized (0.2 μmole scale) on a dual column Cyclone Plus DNA synthesizer (Milligen-Biosearch) and purified using OPC cartridges (Applied Biosystems). Each oligonucleotide (30 μg) was then 5'-phosphorylated using the KinAce-It™ kit from Stratagene. Unincorporated ATP was removed using a Mermaid kit (Bio 101). Appropriate oligonucleotide pairs (1 μg each) were annealed by heating to 65° C., and cooled over a period of 20 minutes to 4° C. The annealed pairs were mixed and ligated together using a DNA ligation kit (Stratagene), according to the manufacturer's instructions.

A 1 μl aliquot of a 100-fold dilution of the ligation mix was subjected to PCR with a pair of primers designed to: 1) incorporate restriction sites appropriate for cloning (XbaI and BamHI at 5' and 3' ends of the gene respectively), 2) introduce a translation initiation codon immediately prior to the first nucleotide of the EDN gene, and 3) incorporate tandem translation termination codons immediately after the last nucleotide of the final codon. After PCR, a product of the required size of 405 base pairs was recovered from an agarose gel using the Geneclean procedure (Bio 101), digested with the appropriate restriction enzymes, and cloned into the bacterial expression vector, pET-11d (Novagen). The composition of the synthetic gene was confirmed by dideoxynucleotide chain terminating sequencing of double-stranded DNA templates using Sequenase II kit (United States Biochemical Corp.).

2. Construction of a Synthetic Gene Encoding (−4)rEDN.

A 5' oligonucleotide was designed to incorporate amino acids, SLHV (SEQ ID NO:16), to be located in positions −4 to −1 of the first amino acid of EDN. The format of the 5' primer oligonucleotide is as follows:

5'-ATATA-TCTAGA-*AATAATTTTGTTTAACTTTAAGAAGGAGATATACAT*-ATG- SEQ ID NO:7

TCACTCCATGTC-*AAACCGCCGCAGTTCACTTGG*-3' where the first 5 base pairs (bp) provide a clamp for the restriction enzyme, the bold sequence is an Xba1 restriction site, the italicized sequence is a modified vector sequence, the underlined ATG is the initiating methionine sequence, the underlined bold sequence codes for SLHV (SEQ ID NO:16) amino acids and the underlined italicized sequence is the first 7 amino acids of EDN.

The 3' primer oligonucleotide is as follows and given in the 5' to 3' orientation:

SEQ ID NO:8

5'-GTTCATCTGGACCGTATCATC-*TAGTAG*-*GGATCC*-GCGCG-3' where the first 21 bps code for the last 7 amino acids of EDN, the italicized sequence codes for 2 stop signals, the bold italicized sequence is the BamHI restriction site and the bold sequence provides a clamp for the restriction enzyme.

The 4 amino acid sequences were attached to the EDN gene by PCR using the following reaction mixture (final concentration in 100 μL reaction volume):

1X reaction buffer (10 mM Tris-HCl, pH 8.3, 50 mM KCl, 1.5 mM $MgCl_2$)

100 μM of each nucleotide 0.5 μM each of the above primers 500 ng/mL EDN DNA

The conditions for PCR were: incubate the reaction mixture at 94° C. for 5 min before beginning the program; adding to the mixture 1 μL AmpliTaq DNA Polymerase; Incubate the reaction mixture at the following temperatures: at 94° C. for 1 min to allow denaturation; at 55° C. for 2 min to allow annealing; at 72° C. for 2 min to permit the extension. The reaction was run for 20 cycles.

After PCR, the reaction was analyzed on a agarose gel and a product of the required size was recovered from the reaction mixture using the Gene Clean II procedure (Bio 101 Inc., La Jolla, Calif.), digested with the appropriate restriction enzymes, and cloned into the bacterial expression vector, pET-11d (Novagen). The composition of the synthetic gene was confirmed by dideoxynucleotide chain terminating sequencing of double-stranded DNA templates using Sequenase II (United States Biochemical Corp.). FIG. 2 shows the comparison of the sequences of the N-termini of rEDN and (−4)rEDN.

3. Ribonuclease Activity of (−4)rEDN The enzymatic activity was measured in a final volume of 0.3 ml containing 0.33 mg/ml yeast tRNA, 0.17 M Tris-HCl, pH7.5, 0.17 mM EDTA, 0.17 mg/ml human serum albumin (Calbiochem) and the appropriate concentration of the ribonucleases (dilutions were made in 0.5 mg/ml human serum albumin). The mixtures were incubated for 15 min at 37° C. before termination with 700 µl 3.4% ice cold perchloric acid. Tubes sat for 10 min on ice before centrifugation in an Eppendorf microcentrifuge for 10 min at 4° C. The absorbance of the supernatants was determined at $A_{260\ nm}$. Absorbance readings of the appropriate blanks were subtracted form assays containing the enzyme.

4. In Vitro Analysis of Cytotoxicity of (−4)rEDN

KS Y-1 cells (ATCC Accession No. 11448) were prepared in concentration of 2500 cells in 0.1 ml) and were plated into each well of a 96 well microtiter plate 24 hours before treatment. The recipe for the RPMI culture medium for the KS Y-1 cells is as follows:

RPMI medium with L-Glutamine (GIBCO-BRL, Gaithersburg, Md.)
10% FBS (GIBCO)
1% Penicillin-Streptomycin (GIBCO)
1% MEM Non-essential Amino Acids 10 mM (100X) (GIBCO)
2% MEM Essential Amino Acids (50X) (GIBCO)
1% MEM Sodium Pyruvate 10 mM (100X) (GIBCO)
1% Nutridoma-HU (Boehringer Mannheim)

On the day of treatment, dilution curves of the buffer control and (−4)rEDN or rEDN were made in sterile dilution buffer (0.5 mg/ml human serum albumin in sterile $H_2O$) and 10 µL applied to the appropriate wells. The plates were incubated at 37° C. in a humidified 5% $CO_2$ incubator for 3 days. Below we present two tests to demonstrate that (−4) rEDN selectively kills KS Y-1 cells:

A). $^{14}C$ Leucine Incorporation;

The serum containing medium was replaced with 100 µL of serum- and Leucine-free RPMI. 0.1 mCi of $^{14}C$ Leucine (in 10 µL) was added and the incubation continued for another 2–4 hrs. The cells were harvested onto glass fiber filters using a PHD cell harvester, washed with $H_2O$, dried with ethanol and counted. The results are expressed as the % of $^{14}C$ leucine incorporation into buffer treated wells, and are shown in FIG. 3. FIG. 3 shows that protein synthesis in KS Y-1 cells is drastically decreased when (−4)rEDN is added to the cells, whereas rEDN does not have a significant impact on the growth of KS Y-1 cells.

Figure 4:
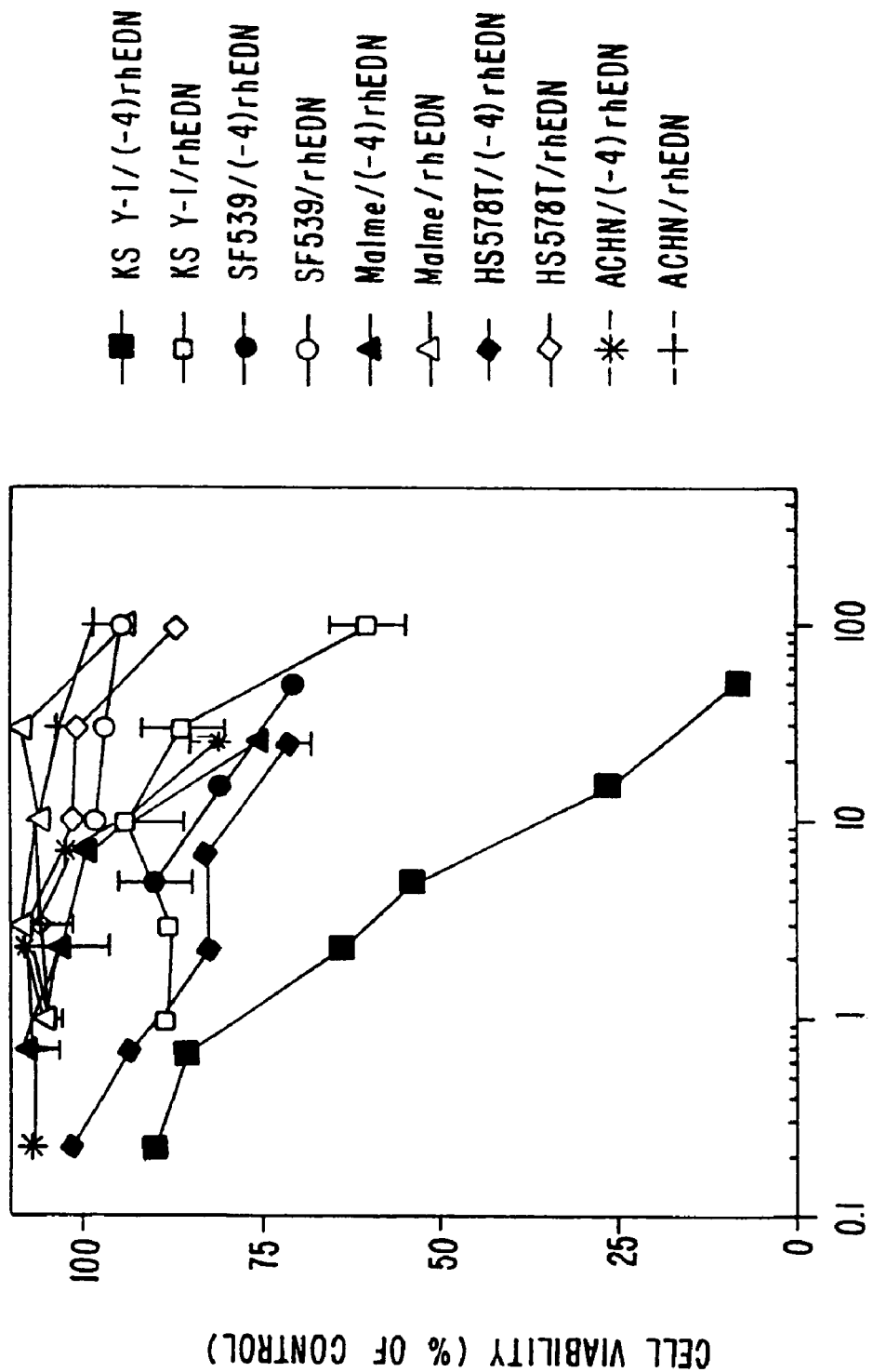
FIG. 4 shows that (−4)rEDN has a specific effect on inhibiting growth of KS Y-1 cells (squares), and it has little impact on the growth of four other cancer cell lines such as SF 539 (circles), Malme (triangles), HS578 T (diamonds), or ACHN (crosses). The WST-1 cell viability was used to assay the cytotoxicity of the various cell lines in the presence of (−4)rhEDN (filled symbols) or rhEDN (open symbols).

B). WST-1 Cell Viability Assay;

10 µL of WST-1 (Boehringer Mannheim, Indianapolis, Ind.) was added directly to each well. The plates were incubated for a further 30–60 min at 37° C. in a humidified 5% $CO_2$ incubator and absorbance at 460 nm determined in a microtiter plate reader. The results are expressed as a % of the buffer treated cells, and are shown in FIG. 4. FIG. 4 shows that (−4)rEDN has a specific effect on inhibiting growth of KS Y-1 cells, and it has little impact on the growth of four other cancer cell lines such as SF 539, Malme, HS578T, or ACHN.

5. Binding of (−4)rhEDN, rhEDN and Onconase to KS Y-1 Cells.

The binding properties of (−4)rhEDN and rhEDN to KS Y-1 cells were tested. The binding of (−4)rhEDN was assessed by measuring the ability of radiolabeled (−4) rhEDN to bind to KS Y-1 cells in the presence and absence of unlabeled onconase. The binding of (−4)rhEDN was compared to the ability of rhEDN to bind to KS-Y1 cells in the presence of onconase as well. See FIG. 5.

Figure 5A:
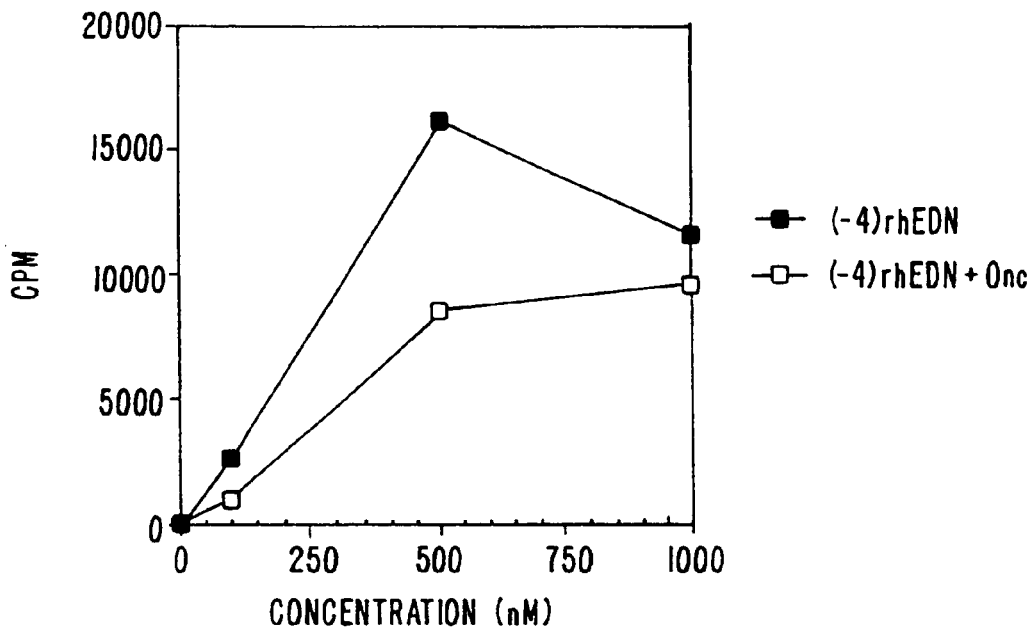
FIG. 5 shows the competition of (−4)rhEDN and rhEDN with onconase for binding to KS Y-1 cells. Varying concentrations of labeled (−4)rhEDN or rhEDN were added to KS Y-1 cells in the presence or absence of onconase. The cells were washed with phosphate-buffered saline and then solubilized with 0.1 N NaOH. Lysates were then counted in a gamma counter. The top panel is a graph of cpm versus the concentration of (−4)rhEDN in the absence of onconase (closed squares) and (−4)rhEDN in the presence of oceans (open squares). The bottom panel is a graph of cpm versus the concentration of rhEDN in the absence of onconase (closed circles) and rhEDN in the presence of onconase (open circles).
Figure 5B:
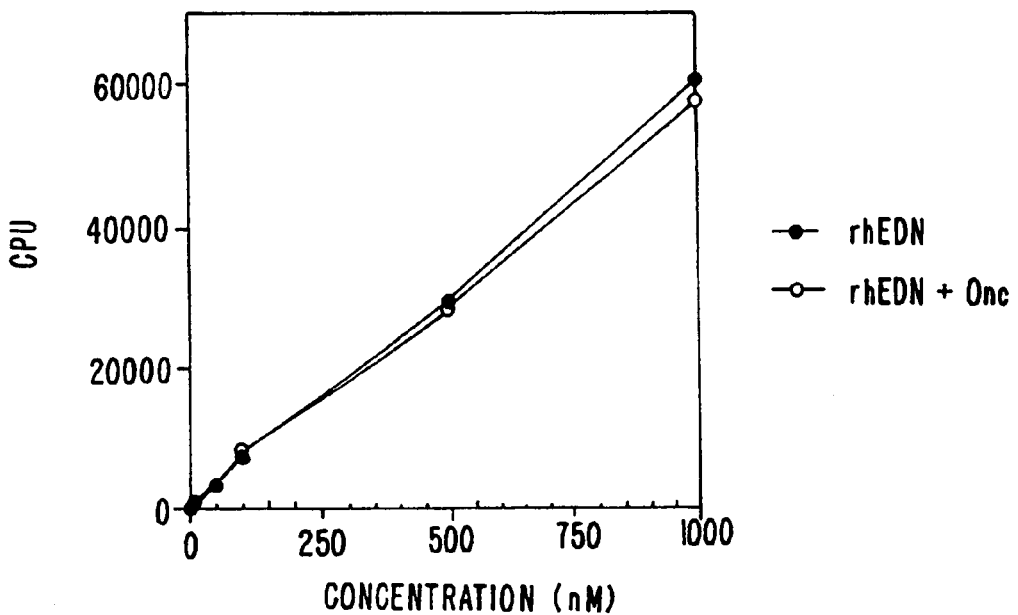

KS Y-1 cells were plated at a density of $4.0\times10^4$ cells/well in a 24-well plate. Twenty-four hours later, the cells were washed twice with phosphate-buffered saline containing 0.1% bovine serum albumin and the appropriate wells pre-treated at 4° C. for 15 min with 100 µM onconase. Varying concentrations of $[^{125}I](-4)$rhEDN (specific activity, 0.25 µCi/µg) or $[^{125}I]$rhEDN (specific activity, 0.32 µC/µg) were added and the incubation continued at 4° C. for 2 hrs. The cells were washed 2 times with phosphate-buffered saline containing 0.1% bovine serum albumin before solubilization for 30 min at 37° C. with 0.1N NaOH. Lysates were then counted in a gamma counter. The results are seen in FIG. 5. The top panel of FIG. 5 shows that the binding of iodinated (−4)rhEDN is saturable is the presence or absence of onconase. The binding of iodinated (−4) rhEDN is partially blocked by onconase. See FIG. 5, top panel. The binding of iodinated rhEDN, on the other hand, is not saturable and is not blocked by onconase. See FIG. 5, bottom panel. The amount of iodinated rhEDN radioactivity does not level off even at 1000 nM. Whereas, the binding of (−4)rhEDN begins to level off around 500 nM.

Figure 6A:
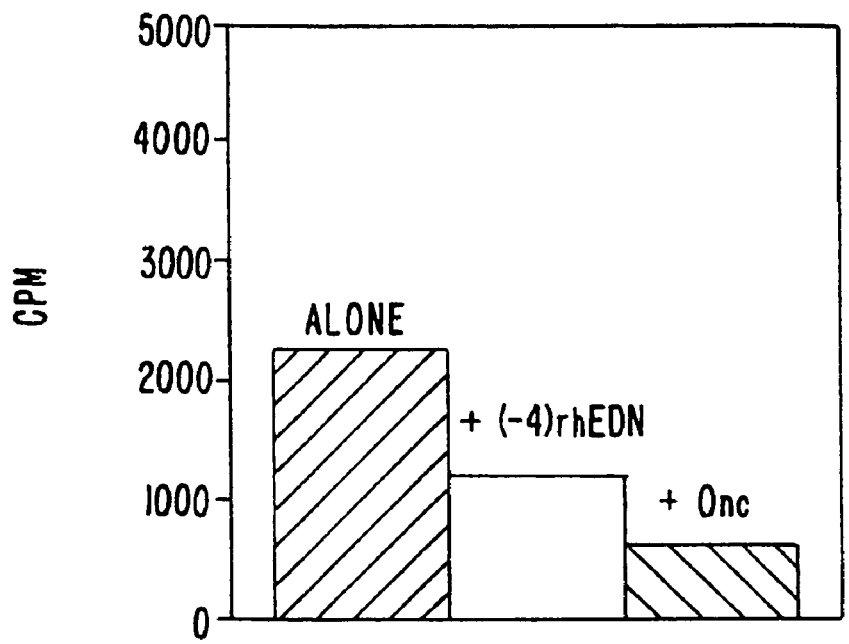
FIG. 6 shows the competition of (−4)rhEDN and rhEDN with (−4)rhEDN, rhEDN, or onconase for binding to KS Y-1 cells. KS Y-1 cells were pretreated with a 50-fold excess of onconase before the addition of labeled (−4)rhEDN or rhEDN. The cells were washed with phosphate-buffered saline and solubilized with 0.1 N NaOH. The lysates were then counted in an gamma counter. The left hand panel is a bar graph of the cpm of labeled (−4)rhEDN as competed with nothing (alone), (−4)rhEDN (cold (−4)rhEDN), and Onc. (onconase). The right hand panel is a bar graph of the cpm of labeled rhEDN as competed with nothing (alone), rhEDN (cold rhEDN), and Onc. (onconase).
Figure 6B:
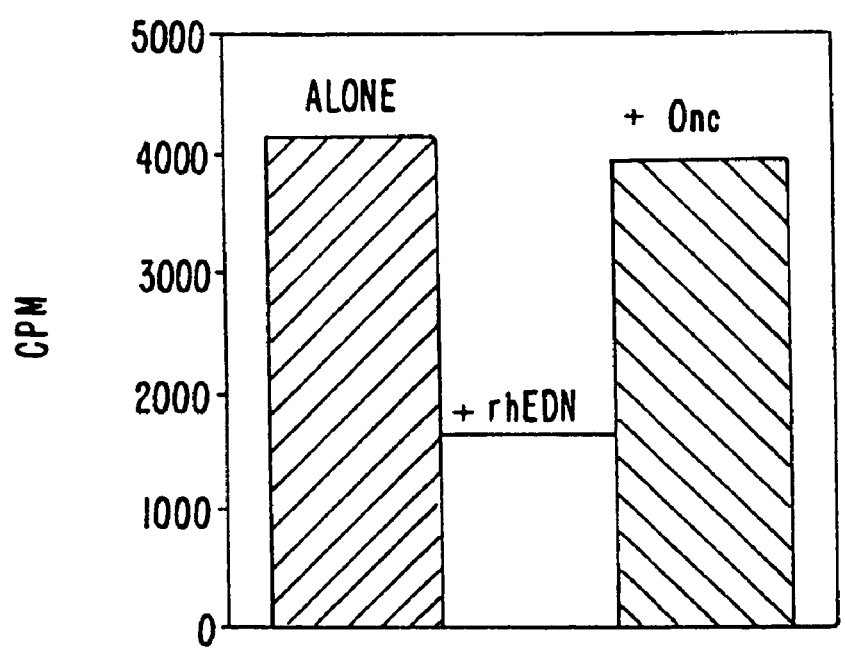

The ability of iodinated (−4)rhEDN or iodinated (−4) rhEDN to bind to KS Y-1 cells was also measured in the presence of buffer, (−4)rhEDN or cold onconase. See FIG. 6, Table I. A scoring system was used for Table I, where 4+ represents the most activity, 1+ the least inactivity, and the (−) indicates inactivity. KS Y-1 cells plated as described in the previous experiment. The KS Y-1 cells were pre-treated with a 50 fold excess of either cold (−4)rhEDN or onconase (for binding of $[^{125}I (-4)$rhEDN) or cold rhEDN or onconase (for binding of $[^{125}I$ rhEDN) for 15 min? at 4° C. Then $[^{125}I](-4)$rhEDN (specific activity, 0.25 µCi/µg) or $[^{125}I]$ rhEDN (specific activity, 0.32 µCi/µg) were added to the respective plate of cells to a final concentration of 100 nM. Incubation was continued for 2 hrs at 4° C. before termination as described above. Onconase interferes with the binding of (−4)rhEDN but not rhEDN to KS Y-1 cells. See FIG. 6, Table I. Both rhEDN or (−4)rhEDN can partially block the binding of labeled rhEDN or (−4)rhEDN, respectively. See FIG. 6, Table I. These data imply that the four amino acids added onto rhEDN modify its binding properties.

6. Cytotoxicity of (−4)rhEDN Towards KS Y-1 Cells.

The cytotoxicity (−4)rhEDN were assayed on KS Y-1 cells. Cytotoxicity was assessed by treating KS Y-1 cells with (−4)rhEDN and rhEDN and measuring protein synthesis inhibition ($[^{14}C]$leucine incorporation into protein after 3 days of treatment). See Example 4A for the method. The results of the cytotoxicity assay are tabulated in Table I. The (−4)rhEDN displays high cytotoxicity against KS Y-1 cells, whereas rhEDN does not exhibit cytotoxicity.

7. Cellular Retention, Release and Uptake of (−4)rhEDN.

Cellular retention and release (intact and degraded) of (−4)rhEDN was tested against KS Y-1 cells. Briefly, KS Y-1 cells were plated in 96-well plates ($1\times10^4$ cells per well) and incubated with 10 µg/ml $[^{125}I](-4)$rhEDN or $[^{125}I]$rhEDN for 2 hrs. The cells were then washed twice with Hank's balanced saline solution to remove unbound protein. Then 200 µL media was added to the cells and the incubation continued at 37° C. At different time points, the amount of $[^{125}I](-4)$rhEDN or $[^{125}I]$rhEDN retained by the cell or released into the medium was determined. Protein retained was determined by solubilizing the cells with 0.1 N NaOH for 30 minutes at 37° C. The level of protein released as intact or degraded was determined by measuring acid-soluble radioactivity released into the media as described by Backer et al. (1983) *Proc. Natl. Acad. Sci., U.S.A.* 80:2166–2170. Briefly, 100 µL media was incubated with an equal volume of 3.25% phosphotungstate in 5% HCl. Radioactivity in the supernatant represents degraded protein while that found in the pellet is intact protein. The results are indicated in Table I.

To determine cellular uptake, KS Y-1 cells ($1 \times 10^4$ cells per well) were treated with 10 µg/ml [$^{125}$I](–4)rhEDN or [$^{125}$I]rhEDN. At different time points, the media was removed, the cells washed twice with Hank's balanced saline solution, 100 µL 0.1 N NaOH added, and the cells solubilized as described with 0.1 N NaOH. The amount of radioactivity associated with the solubilized cell is an indication of cellular uptake of protein. See Table I.

These results indicate that (–4)rhEDN is able to bind to some molecular target on the cell surface that causes it to be productively routed into the cytosol. rhEDN binds more total counts to the surface and is internalized, but most of the counts are released as degraded protein. See Table I. In contrast, (–4)rhEDN does not result in as much total binding as rhEDN to the cell surface, but internalization of (–4)rhEDN does not result in the counts being released as degraded protein. See Table I. Rather the counts are retained by the cell. See Table I. This suggests that the amino terminal modification of rhEDN to form (–4)rhEDN causes the molecule to be routed differently than rhEDN.

TABLE I

Comparison of the properties of (–4)rhEDN and rhEDN

|  | rhEDN | (–4)rhEDN |
|---|---|---|
| Binding (total) | ++++ | + |
| Binding (Ono pathway) | ---- | ++ |
| Cellular uptake | ++++ | + |
| Cellular retention | ++++ | + |
| Cellular release (intact) | ++ | ++++ |
| Cellular release (degraded) | ++ | ---- |
| Cytotoxicity | ---- | ++++ |

8. Cytotoxicity of (–4)rhEDN Towards HUVEC Cells.

The $^{14}$C leucine incorporation assay, (See Example 4A), was used to measure the cytotoxicity of (–4)rhEDN towards three different endothelial cells: HBV immortalized HUVECs (Human umbilical vein endothelial cells); primary HUVECs; and tumorigenic Ki-ras transformed HUVECs. The HBV immortalized HUVECs were immortalized with the E6/B7 genes of human papilloma virus. They maintain differentiated endothelial cell characteristics. See Rhim, J. et al. (1998) *Carcinogenesis*, 19: 101–109. The HBV immortalized HUVECs were then transformed into tumorigenic endothelial cells with the activated oncogene Ki-ras to create the tumorigenic Ki-ras transformed HUVECs. The cells were treated with varying concentrations of (–4)rhEDN for 3 days and cytotoxicity was assessed as described in Example 4A.

Figure 7:
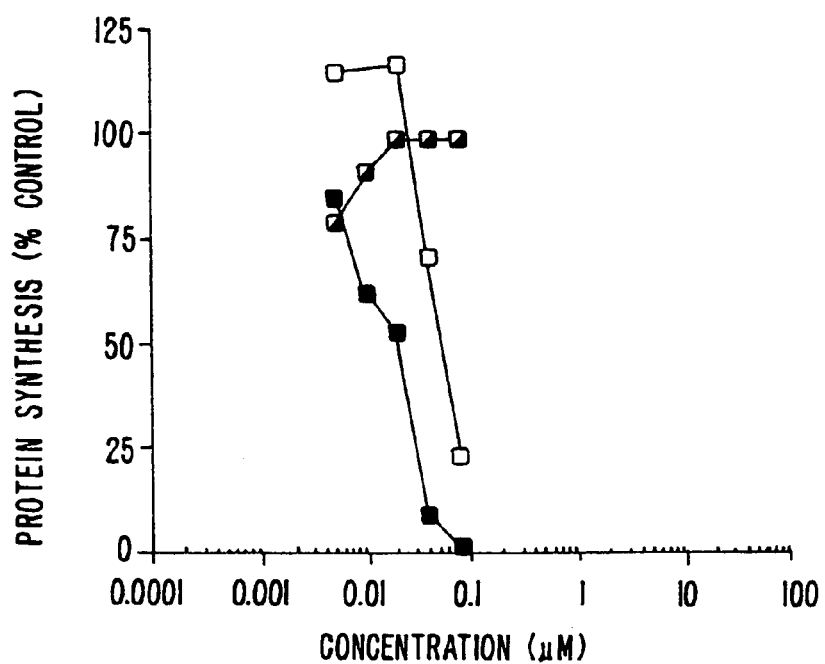
FIG. 7 shows the cytotoxicity of (−4)rhEDN towards three different endothelial cells. The $^{14}$C Leucine incorporation assay was used to measure the cytotoxicity of (−4) rhEDN towards Human umbilical vein endothelial cells.

The (–4)rhEDN exhibited cytotoxicity against the HBV immortalized HUVECs and the tumorigenic Ki-ras transformed HUVECs. See FIG. 7. The (–4)rhEDN was able to inhibit more than 50% of the protein synthesis seen with control samples at less than 100 nM (–4)rhEDN for both HBV immortalized HUVECs and the tumorigenic Ki-ras transformed HUVECs. See FIG. 7. The primary HUVECs did not appear to be inhibited by the (–4)rhEDN. See FIG. 7. Thus, the (–4)rhEDN exhibits activity against rapidly growing human endothelial cell lines but not primary endothelial cells. This may indicate that (–4)rhEDN may have specificity for tumor endothelium and thus potential to inhibit the growth of tumors by inhibiting the growth of tumor endothelium.

9. Expression and Assays of (–4)rhEDN as a Phage Display Protein

The phage display technology can be used to express the (–4)rhEDN on the surface of a phage. Phage bearing only peptides can safely be injected into mice. Arap, W. et al. (1998) *Science* 279: 377–380. Thus the recombinant phage bearing (–4)rhEDN may prove useful for killing certain cell types in vivo.

Figure 8:
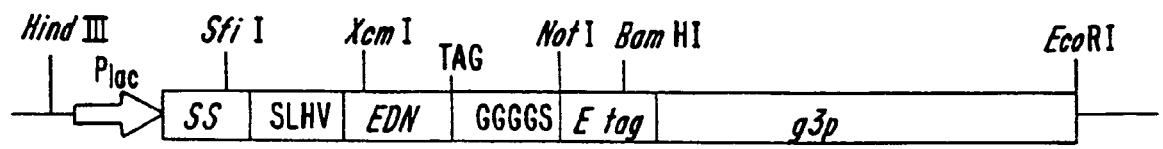
FIG. 8 shows a map of the (−4)rhEDN—g3p fusion construct. A DNA fragment encoding (−4)rhEDN was cloned into the phagemid vector pCANTAB5E (Pharmacia). The pCANTAB5E vector is comprised of a leader sequence (SS), followed by the peptide SLHV (SEQ ID NO:16) which is fused to the EDN coding region. The sequence denoted TAG is an amber stop codon. The sequence GGGGS (SEQ ID NO:17) is a peptide sequence which was inserted to allow more flexibility for the folding of (−4)rhEDN. The sequence g3p refers to the g3p coding sequence.

A). Construction of the Phage Display Vector for the (–4) rhEDN Protein;

A DNA fragment encoding (–4)rhEDN was cloned into the phagemid vector pCANTAB5E (Pharmacia). This vector permits the expression of genes cloned into it as a g3p fusion protein. The pCANTAB5E vector is comprised of a leader sequence (SS) that directs secretion of the g3p fusion protein to the surface of the bacteria. See FIG. 8. The E tag consists of a 21 amino acid peptide to which a commercial antibody is available for detecting expression. The sequence denoted TAG is an amber stop codon. See FIG. 8. The TAG in the commercial vector was changed from its position behind the Etag to a new position behind the signal peptide EDN for release of the protein during certain expression systems. A GGGGS (SEQ ID NO:17) peptide sequence was inserted between the (–4)rhEDN and the g3p protein to allow more flexibility of folding the (–4)rhEDN. The four amino acids attached to the to amino terminus of rhEDN are SLHV (SEQ ID NO:16).

B). Production and Isolation of Phage Bearing (–4)rhEDN;

The (–4) rhEDN-g3p fusion construct in phagemid was introduced into *E. coli* TG1 cells by transformation and grown on Minimal Medium agar plates containing 100 mg/L ampicillin at 37° C. for 2 days. Around 3–5 well-separated single colonies were selected and grown in 5 ml 2×YT-AG medium at 37° C. with 250 rpm shaking for 3–5 hr to an $OD_{600}$~0.5. Then, M13KO7 helper phage were then added to the culture to a concentration of $2 \times 10^9$ pful/ml. After a 1 hour co-incubation at 37° C. with 250 rpm shaking, the culture was centrifuged (1,000×g) at 20° C. for 15 min. The pelleted cells were resuspended in 50 ml 2×YT (Ampicillin 100 µg/ml and Kanamycin 25 µg/ml) at 37° C. with 250 rpm shaking to $OD_{600}$~0.5, then scaled up to 800–1000 ml and grown at 37° C. with 250 rpm shaking, overnight. The culture was then centrifuged (11,300×g) at 4° C. for 30 mm and the supernatant containing the recombinant phage was collected. To the supernatant, 1/5 volume of $PEG_{8000}$/NaCl was added and incubated at 4° C. or on ice for 3 hr. The solution was centrifuged (14,300×g) at 4° C. for 30 min. The precipitated phage were re-suspended in PBS and stored at 4° C.

C). Assay of the Recombinant (–4)rhEDN Phage for RNase Enzymatic Activity;

The tRNA RNase assay was used to assay the soluble (–4)rhEDN expressed as a g3p fusion protein on phage. See yeast tRNA ribonuclease assay in Example 3. The ribonuclease activity of rhEDN was assayed as a positive control for the assay. The rhEDN was diluted with HSA Buffer to 0.00001; 0.0001; 0.001; 0.01; 0.1 ng/µl. The PEG precipitated phage above was diluted to $4.5 \times 10^{10}$ cfu/ml. To 150 µl reaction solution (50 µl tRNA, 1 µg/µl in $H_2O$; 50 µl HSA buffer, 0.5 mg/ml in $H_2O$, and 50 µl RNase Assay Buffer, pH 7.5), 10 µl of various dilutions of rhEDN protein or 10 µl phage was added and incubated at 37° C. for 16 hrs. The reaction was terminated by adding 350 µl of 3.4% ice-cold perchloric acid and incubated on ice for 10 min. The solution was then centrifuged for 10 min in microcentrifuge at full speed. The supernatant was transferred to a fresh tube and $OD_{260}$ was measured.

Figure 9A:
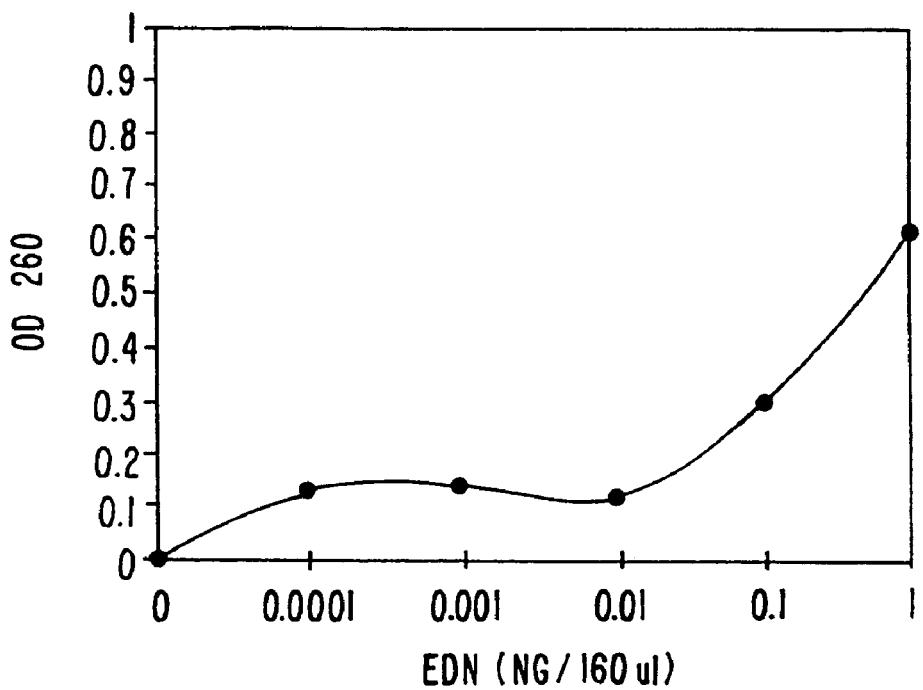
FIG. 9 shows the RNase activity of (−4)rhEDN expressed as a g3p fusion protein on phage. The tRNA RNase assay was used as described in the Methods for soluble (−4) rhEDN. The left hand panel is a positive control assay for ribonuclease activity with soluble rhEDN. The right hand panel is a bar graph of control phage (M13KO7) as compared to SigEDN phage (the phage bearing (−4)rhEDN).
Figure 9B:
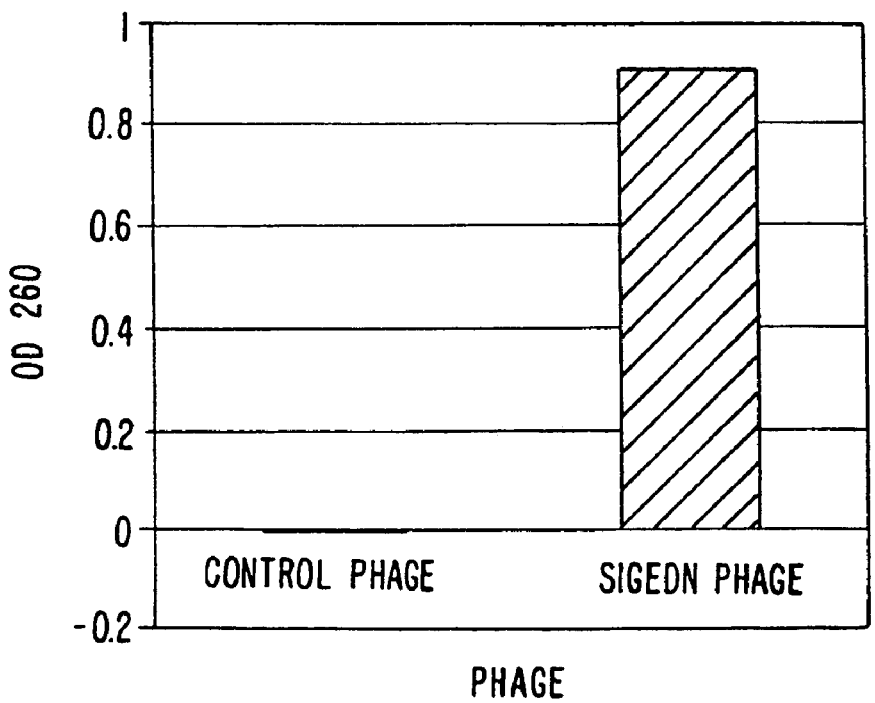

The positive control of rhEDN, shows that the assay could measure ribonuclease activity. See. FIG. 9, left-hand panel. The phage displaying the (–4)rhEDN exhibited ribonuclease activity. See FIG. 9, right-hand panel. The control phage, however, do not express RNase activity. See FIG. 9, right-hand panel. These results indicate the (–4)rhEDN molecule that is expressed on the phage as a g3p fusion protein still retains ribonuclease activity.

Figure 10:
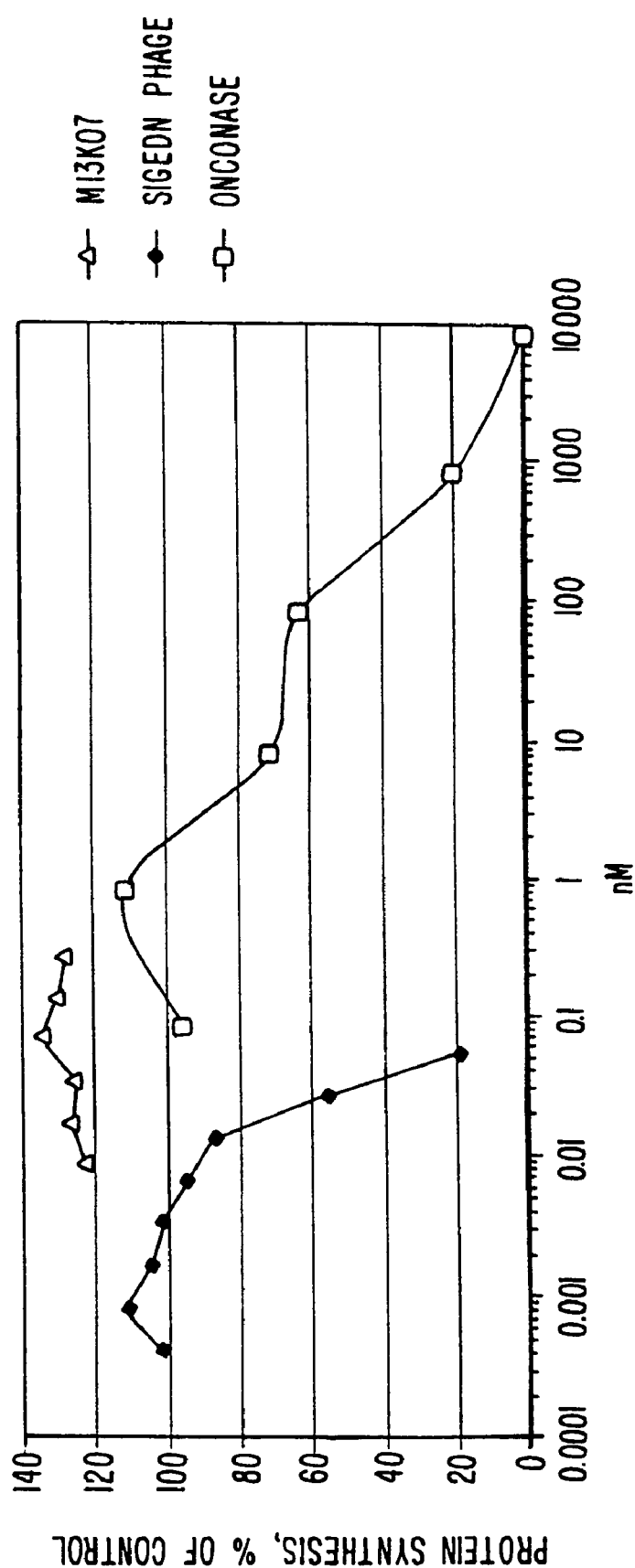
FIG. 10 shows the cytotoxicity of the phage displaying (−4)rhEDN against Lewis Lung cells. The methods for the $^{14}C$ Leucine incorporation assay are the same as described for soluble (−4)rhEDN in Example 4A. The open triangles are M13KO7, the filled diamonds are SigEDN phage ((−4) rhEDN phage), and the open squares are onconase.

10). Cytotoxicity of the Phage Displaying the (–4)rhEDN Against Lewis Lung Cells and KS Y-1 Cells;

The (–4)rhEDN was assayed for cytotoxicity on Lewis lung cells (model for angiogenesis and KS Y-1 cells. The methods for the protein synthesis assay are the same as described already for soluble (–4)rhEDN on KS Y-1 cells. See Example 4A. Lewis lung and KS Y-1 cells were plated (2500 cells in 0.1 ml per well) into the wells of a 96-well microtiter plate 24 hr before treatment. PEG concentrated phage was diluted in HSA buffer to a 2-fold dilution series and added to the wells and incubated at 37° C. in a humidified, 5% $CO_2$ incubator for 3 days. Both the M13K07 phage and the phage bearing (–4)rhEDN were assayed for their cytotoxicity. Onconase was also assayed as a positive control for cytotoxicity. PBS containing 0.1 mCi of [$^{14}$C] leucine was added for 4 hours, and the cells were then collected onto glass fiber filters using a PHD cell harvester. The new synthesized protein was then measured by using a liquid scintillation counter. The results were expressed as a percentage of radiolabeled-leucine incorporation in HSA buffer-treated cells. See FIG. 10. The M13K07 phage did not exhibit cytotoxicity. The (–4)rhEDN phage (denoted SigEDN phage in FIG. 10) were able to inhibit the protein synthesis in Lewis lung cells greater than 80% at a concentration less than 0.1 nM. Thus, (–4)rhEDN is cytotoxic towards Lewis Lung cells when expressed as a fusion protein in a phage display system. The (–4)rhEDN phage were also cytotoxic against KS Y-1 cells. Data not shown.

10. In Vivo Analysis of Cytotoxicity of (–4)rEDN

KS Y-1 cells ($5\times10^5$) are injected subcutaneously into immunodeficient (Xid) beige mice. The mice then receive intralesional injections of various preparations of (–4)rEDN at doses of 100 IU in a volume of 0.2 ml each day for seven days. The animals are sacrificed after three to four weeks and examined grossly and microscopically for the presence of tumor, angiogenesis, and metastasis.

11. Treating Kaposi's Sarcoma Patients with (–4)rEDN

This example demonstrates a therapeutic use of (–4)rEDN in treating Kaposi's sarcoma patients. Male persons of average weight (about 70 kg) are selected as patients. The patients possess the symptom of Kaposi's sarcoma including nodular cutaneous lesions in their skin.

The treatment consists of intralesional injection of the (−4)rEDN mixed with 0.4% saline. The dosage of (−4)rEDN is set at 1000 IU, and (−4)rEDN is mixed with saline as a carrier to form a pharmaceutical composition. In each patient, two lesions are injected with the composition three times a week for two weeks. The volume of the injection is set at 0.2 ml for. The injection is repeated for two weeks. Patients are evaluated by physical examination of the lesions, and questioned for any signs or symptoms prior to treatment at 2 weeks and 4 weeks. Results are recorded in charts for comparison.

All publications, including patents and patent applications, mentioned herein above are hereby incorporated by reference.

The foregoing invention has been described in some detail for purposes of clarity and understanding. It will also be obvious that various combinations in form and detail can be made without departing from the scope of the invention.

---

What is claimed is:

1. An isolated RNase A superfamily polypeptide having an N-terminus of the sequence: $X^1X^2SLX^3V$ (SEQ ID NO:9), wherein $X^1$ represents methionine, $X^2$ represents glycine, and $X^3$ represents any amino acid residue, said RNase A superfamily polypeptide being selectively toxic to a proliferating endothelial cell and having at least 90% sequence identity to SEQ ID NO:4.

2. An isolated RNase A superfamily polypeptide of claim 1 having SEQ ID NO:4.

3. An isolated RNase A superfamily polypeptide of claim 1 wherein the N-terminus is MGSLHV (SEQ ID NO:10).

4. An isolated RNase A superfamily polypeptide of claim 1 wherein the N-terminus is attached to the eosinophil derived neurotoxin (EDN) protein.

5. An isolated RNase A superfamily polypeptide of claim 1 wherein the proliferating endothelial cell is a neoplastic endothelial cell.

6. An isolated RNase A superfamily polypeptide of claim 1 wherein the proliferating endothelial cell is a non-neoplastic endothelial cell.

7. An isolated RNase A superfamily polypeptide of claim 5 wherein the neoplastic endothelial cell is a Kaposi sarcoma KS Y-1 cell.

8. An isolated RNase A superfamily polypeptide of claim 5 wherein the neoplastic endothelial cell is a KS Y-3 cell.

9. An isolated RNase A superfamily polypeptide of claim 5 wherein the neoplastic endothelial cell is selected from the group consisting of KS 1, KS 2, KS 3, KS 4, KS 5, and KS 6 cells.

10. A pharmaceutical composition comprising
   a. a unit dosage RNase A superfamily polypeptide comprising an N-terminus of the sequence: $X^1X^2SLX^3V$ (SEQ ID NO:9), wherein $X^1$ represents methionine, $X^2$ represents glycine, and $X^3$ represents any amino acid residue, said RNase A superfamily polypeptide being selectively toxic to a proliferating endothelial cell and having at least 90% sequence identity to SEQ ID NO:4; and
   b. a pharmaceutically acceptable carrier.

* * * * *

SEQUENCE LISTING

```
<160> NUMBER OF SEQ ID NOS: 25

<210> SEQ ID NO 1
<211> LENGTH: 417
<212> TYPE: DNA
<213> ORGANISM: Artificial Sequence
<220> FEATURE:
<223> OTHER INFORMATION: Description of Artificial Sequence:recombinant
      eosinophil derived neurotoxin with and added 4
      amino acid sequence at its amino terminus
      (r(-4)EDN)
<220> FEATURE:
<221> NAME/KEY: CDS
<222> LOCATION: (1)..(417)

<400> SEQUENCE: 1 atg tca ctc cat gtc aaa ccg ccg cag ttc act tgg gct cag tgg ttc       48
Met Ser Leu His Val Lys Pro Pro Gln Phe Thr Trp Ala Gln Trp Phe
  1               5                  10                  15 gaa act cag cat atc aac atg act tct cag cag tgc act aac gct atg       96
Glu Thr Gln His Ile Asn Met Thr Ser Gln Gln Cys Thr Asn Ala Met
             20                  25                  30 cag gtt atc aac aac tac cag cgt cgt tgc aaa aac cag aac act ttc      144
Gln Val Ile Asn Asn Tyr Gln Arg Arg Cys Lys Asn Gln Asn Thr Phe
```

```
                 35                  40                  45
ctg ctg act act ttc gct aac gtt gtt aac gtt tgc ggt aac ccg aac        192
Leu Leu Thr Thr Phe Ala Asn Val Val Asn Val Cys Gly Asn Pro Asn
     50                  55                  60 atg act tgc ccg tct aac aaa act cgt aaa aac tgc cat cat tct ggt        240
Met Thr Cys Pro Ser Asn Lys Thr Arg Lys Asn Cys His His Ser Gly
 65                  70                  75                  80 tct cag gtt ccg ctg atc cat tgc aac ctg act act ccg tct ccg cag        288
Ser Gln Val Pro Leu Ile His Cys Asn Leu Thr Thr Pro Ser Pro Gln
                 85                  90                  95 aac atc tct aac tgc cgt tac gct cag act ccg gct aac atg ttc tac        336
Asn Ile Ser Asn Cys Arg Tyr Ala Gln Thr Pro Ala Asn Met Phe Tyr
            100                 105                 110 atc gtt gct tgc gac aac cgt gac cag cgt cgt gac ccg ccg cag tac        384
Ile Val Ala Cys Asp Asn Arg Asp Gln Arg Arg Asp Pro Pro Gln Tyr
        115                 120                 125 ccg gtt gtt ccg gtt cat ctg gac cgt atc atc                            417
Pro Val Val Pro Val His Leu Asp Arg Ile Ile
    130                 135

<210> SEQ ID NO 2
<211> LENGTH: 139
<212> TYPE: PRT
<213> ORGANISM: Artificial Sequence
<220> FEATURE:
<223> OTHER INFORMATION: Description of Artificial Sequence:recombinant
      eosinophil derived neurotoxin with and added 4
      amino acid sequence at its amino terminus
      (r(-4)EDN)

<400> SEQUENCE: 2

Met Ser Leu His Val Lys Pro Pro Gln Phe Thr Trp Ala Gln Trp Phe
 1               5                  10                  15

Glu Thr Gln His Ile Asn Met Thr Ser Gln Gln Cys Thr Asn Ala Met
                20                  25                  30

Gln Val Ile Asn Asn Tyr Gln Arg Arg Cys Lys Asn Gln Asn Thr Phe
            35                  40                  45

Leu Leu Thr Thr Phe Ala Asn Val Val Asn Val Cys Gly Asn Pro Asn
    50                  55                  60

Met Thr Cys Pro Ser Asn Lys Thr Arg Lys Asn Cys His His Ser Gly
 65                  70                  75                  80

Ser Gln Val Pro Leu Ile His Cys Asn Leu Thr Thr Pro Ser Pro Gln
                85                  90                  95

Asn Ile Ser Asn Cys Arg Tyr Ala Gln Thr Pro Ala Asn Met Phe Tyr
            100                 105                 110

Ile Val Ala Cys Asp Asn Arg Asp Gln Arg Arg Asp Pro Pro Gln Tyr
        115                 120                 125

Pro Val Val Pro Val His Leu Asp Arg Ile Ile
    130                 135

<210> SEQ ID NO 3
<211> LENGTH: 420
<212> TYPE: DNA
<213> ORGANISM: Artificial Sequence
<220> FEATURE:
<223> OTHER INFORMATION: Description of Artificial Sequence:recombinant
      eosinophil derived neurotoxin with an added 5
      amino acid sequence at its amino terminus
      (r(-5)EDN)
<220> FEATURE:
<221> NAME/KEY: CDS
<222> LOCATION: (1)..(420)
```

<400> SEQUENCE: 3

```
atg ggt tca ctc cat gtc aaa ccg ccg cag ttc act tgg gct cag tgg       48
Met Gly Ser Leu His Val Lys Pro Pro Gln Phe Thr Trp Ala Gln Trp
 1               5                  10                  15 ttc gaa act cag cat atc aac atg act tct cag cag tgc act aac gct       96
Phe Glu Thr Gln His Ile Asn Met Thr Ser Gln Gln Cys Thr Asn Ala
                 20                  25                  30 atg cag gtt atc aac aac tac cag cgt cgt tgc aaa aac cag aac act      144
Met Gln Val Ile Asn Asn Tyr Gln Arg Arg Cys Lys Asn Gln Asn Thr
             35                  40                  45 ttc ctg ctg act act ttc gct aac gtt gtt aac gtt tgc ggt aac ccg      192
Phe Leu Leu Thr Thr Phe Ala Asn Val Val Asn Val Cys Gly Asn Pro
         50                  55                  60 aac atg act tgc ccg tct aac aaa act cgt aaa aac tgc cat cat tct      240
Asn Met Thr Cys Pro Ser Asn Lys Thr Arg Lys Asn Cys His His Ser
 65                  70                  75                  80 ggt tct cag gtt ccg ctg atc cat tgc aac ctg act act ccg tct ccg      288
Gly Ser Gln Val Pro Leu Ile His Cys Asn Leu Thr Thr Pro Ser Pro
                 85                  90                  95 cag aac atc tct aac tgc cgt tac gct cag act ccg gct aac atg ttc      336
Gln Asn Ile Ser Asn Cys Arg Tyr Ala Gln Thr Pro Ala Asn Met Phe
                100                 105                 110 tac atc gtt gct tgc gac aac cgt gac cag cgt cgt gac ccg ccg cag      384
Tyr Ile Val Ala Cys Asp Asn Arg Asp Gln Arg Arg Asp Pro Pro Gln
            115                 120                 125 tac ccg gtt gtt ccg gtt cat ctg gac cgt atc atc                      420
Tyr Pro Val Val Pro Val His Leu Asp Arg Ile Ile
        130                 135                 140

<210> SEQ ID NO 4
<211> LENGTH: 140
<212> TYPE: PRT
<213> ORGANISM: Artificial Sequence
<220> FEATURE:
<223> OTHER INFORMATION: Description of Artificial Sequence:recombinant
      eosinophil derived neurotoxin with an added 5
      amino acid sequence at its amino terminus
      (r(-5)EDN)

<400> SEQUENCE: 4

Met Gly Ser Leu His Val Lys Pro Pro Gln Phe Thr Trp Ala Gln Trp
 1               5                  10                  15

Phe Glu Thr Gln His Ile Asn Met Thr Ser Gln Gln Cys Thr Asn Ala
                 20                  25                  30

Met Gln Val Ile Asn Asn Tyr Gln Arg Arg Cys Lys Asn Gln Asn Thr
             35                  40                  45

Phe Leu Leu Thr Thr Phe Ala Asn Val Val Asn Val Cys Gly Asn Pro
         50                  55                  60

Asn Met Thr Cys Pro Ser Asn Lys Thr Arg Lys Asn Cys His His Ser
 65                  70                  75                  80

Gly Ser Gln Val Pro Leu Ile His Cys Asn Leu Thr Thr Pro Ser Pro
                 85                  90                  95

Gln Asn Ile Ser Asn Cys Arg Tyr Ala Gln Thr Pro Ala Asn Met Phe
                100                 105                 110

Tyr Ile Val Ala Cys Asp Asn Arg Asp Gln Arg Arg Asp Pro Pro Gln
            115                 120                 125

Tyr Pro Val Val Pro Val His Leu Asp Arg Ile Ile
        130                 135                 140
```

<210> SEQ ID NO 5
<211> LENGTH: 402
<212> TYPE: DNA
<213> ORGANISM: Artificial Sequence
<220> FEATURE:
<223> OTHER INFORMATION: Description of Artificial Sequence:recombinant
      eosinophil derived neurotoxin (rEDN)
<220> FEATURE:
<221> NAME/KEY: CDS
<222> LOCATION: (1)..(402)

<400> SEQUENCE: 5

```
aaa ccg ccg cag ttc act tgg gct cag tgg ttc gaa act cag cat atc      48
Lys Pro Pro Gln Phe Thr Trp Ala Gln Trp Phe Glu Thr Gln His Ile
  1               5                  10                  15 aac atg act tct cag cag tgc act aac gct atg cag gtt atc aac aac      96
Asn Met Thr Ser Gln Gln Cys Thr Asn Ala Met Gln Val Ile Asn Asn
             20                  25                  30 tac cag cgt cgt tgc aaa aac cag aac act ttc ctg ctg act act ttc     144
Tyr Gln Arg Arg Cys Lys Asn Gln Asn Thr Phe Leu Leu Thr Thr Phe
         35                  40                  45 gct aac gtt gtt aac gtt tgc ggt aac ccg aac atg act tgc ccg tct     192
Ala Asn Val Val Asn Val Cys Gly Asn Pro Asn Met Thr Cys Pro Ser
     50                  55                  60 aac aaa act cgt aaa aac tgc cat cat tct ggt tct cag gtt ccg ctg     240
Asn Lys Thr Arg Lys Asn Cys His His Ser Gly Ser Gln Val Pro Leu
 65                  70                  75                  80 atc cat tgc aac ctg act act ccg tct ccg cag aac atc tct aac tgc     288
Ile His Cys Asn Leu Thr Thr Pro Ser Pro Gln Asn Ile Ser Asn Cys
                 85                  90                  95 cgt tac gct cag act ccg gct aac atg ttc tac atc gtt gct tgc gac     336
Arg Tyr Ala Gln Thr Pro Ala Asn Met Phe Tyr Ile Val Ala Cys Asp
            100                 105                 110 aac cgt gac cag cgt cgt gac ccg ccg cag tac ccg gtt gtt ccg gtt     384
Asn Arg Asp Gln Arg Arg Asp Pro Pro Gln Tyr Pro Val Val Pro Val
        115                 120                 125 cat ctg gac cgt atc atc                                             402
His Leu Asp Arg Ile Ile
    130
```

<210> SEQ ID NO 6
<211> LENGTH: 134
<212> TYPE: PRT
<213> ORGANISM: Artificial Sequence
<220> FEATURE:
<223> OTHER INFORMATION: Description of Artificial Sequence:recombinant
      eosinophil derived neurotoxin (rEDN)

<400> SEQUENCE: 6

```
Lys Pro Pro Gln Phe Thr Trp Ala Gln Trp Phe Glu Thr Gln His Ile
  1               5                  10                  15

Asn Met Thr Ser Gln Gln Cys Thr Asn Ala Met Gln Val Ile Asn Asn
             20                  25                  30

Tyr Gln Arg Arg Cys Lys Asn Gln Asn Thr Phe Leu Leu Thr Thr Phe
         35                  40                  45

Ala Asn Val Val Asn Val Cys Gly Asn Pro Asn Met Thr Cys Pro Ser
     50                  55                  60

Asn Lys Thr Arg Lys Asn Cys His His Ser Gly Ser Gln Val Pro Leu
 65                  70                  75                  80

Ile His Cys Asn Leu Thr Thr Pro Ser Pro Gln Asn Ile Ser Asn Cys
                 85                  90                  95
```

```
Arg Tyr Ala Gln Thr Pro Ala Asn Met Phe Tyr Ile Val Ala Cys Asp
        100                 105                 110

Asn Arg Asp Gln Arg Arg Asp Pro Pro Gln Tyr Pro Val Val Pro Val
            115                 120                 125

His Leu Asp Arg Ile Ile
        130

<210> SEQ ID NO 7
<211> LENGTH: 83
<212> TYPE: DNA
<213> ORGANISM: Artificial Sequence
<220> FEATURE:
<223> OTHER INFORMATION: Description of Artificial Sequence:5' primer
      oligonucleotide

<400> SEQUENCE: 7
atatatctag aaataatttt gtttaacttt aagaaggaga tatacatatg tcactccatg      60
tcaaaccgcc gcagttcact tgg                                             83

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence:3' primer
      oligonucleotide

<400> SEQUENCE: 8
gttcatctgg accgtatcat ctagtaggga tccgcgcg                             38

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide
<220> FEATURE:
<221> NAME/KEY: MOD_RES
<222> LOCATION: (1)
<223> OTHER INFORMATION: Met at position 1 may be present or absent
<220> FEATURE:
<221> NAME/KEY: MOD_RES
<222> LOCATION: (2)
<223> OTHER INFORMATION: Gly at position 2 may be present or absent
<220> FEATURE:
<221> NAME/KEY: MOD_RES
<222> LOCATION: (5)
<223> OTHER INFORMATION: Xaa = any amino acid

<400> SEQUENCE: 9

Met Gly Ser Leu Xaa Val
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide

<400> SEQUENCE: 10

Met Gly Ser Leu His Val
  1               5

<210> SEQ ID NO 11
```

-continued

```
<211> LENGTH: 5
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide

<400> SEQUENCE: 11

Met Ser Leu His Val
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide
<220> FEATURE:
<221> NAME/KEY: MOD_RES
<222> LOCATION: (5)
<223> OTHER INFORMATION: Xaa = any amino acid

<400> SEQUENCE: 12

Met Gly Ser Leu Xaa Val
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide
<220> FEATURE:
<221> NAME/KEY: MOD_RES
<222> LOCATION: (4)
<223> OTHER INFORMATION: Xaa = any amino acid

<400> SEQUENCE: 13

Met Ser Leu Xaa Val
 1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide
<220> FEATURE:
<221> NAME/KEY: MOD_RES
<222> LOCATION: (4)
<223> OTHER INFORMATION: Xaa = any amino acid

<400> SEQUENCE: 14

Gly Ser Leu Xaa Val
 1               5

<210> SEQ ID NO 15
<211> LENGTH: 4
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide
<220> FEATURE:
<221> NAME/KEY: MOD_RES
<222> LOCATION: (3)
<223> OTHER INFORMATION: Xaa = any amino acid
```

-continued

```
<400> SEQUENCE: 15

Ser Leu Xaa Val
 1

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence:N-terminus
      of modified RNAse A superfamily polypeptide

<400> SEQUENCE: 16

Ser Leu His Val
 1

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence:peptide
      sequence inserted to allow more flexibility for
      the folding of (-4)rhEDN

<400> SEQUENCE: 17

Gly Gly Gly Gly Ser
 1               5

<210> SEQ ID NO 18
<211> LENGTH: 111
<212> TYPE: PRT
<213> ORGANISM: Rana catesbeiana
<220> FEATURE:
<223> OTHER INFORMATION: frog lectin from Rana catesbeiana

<400> SEQUENCE: 18

Glu Asn Trp Ala Thr Phe Gln Gln Lys His Ile Ile Asn Thr Pro Ile
 1               5                  10                  15

Ile Asn Cys Asn Thr Ile Met Asp Asn Asn Ile Tyr Ile Val Gly Gly
                20                  25                  30

Gln Cys Lys Arg Val Asn Thr Phe Ile Ile Ser Ser Ala Thr Thr Val
            35                  40                  45

Lys Ala Ile Cys Thr Gly Val Ile Asn Met Asn Val Leu Ser Thr Thr
        50                  55                  60

Arg Phe Gln Leu Asn Thr Cys Thr Arg Thr Ser Ile Thr Pro Arg Pro
 65                  70                  75                  80

Cys Pro Tyr Ser Ser Arg Thr Glu Thr Asn Tyr Ile Cys Val Lys Cys
                85                  90                  95

Glu Asn Gln Tyr Pro Val His Phe Ala Gly Ile Gly Arg Cys Pro
            100                 105                 110

<210> SEQ ID NO 19
<211> LENGTH: 104
<212> TYPE: PRT
<213> ORGANISM: Homo sapiens
<220> FEATURE:
<223> OTHER INFORMATION: eosinophil derived neurotoxin protein (EDN)

<400> SEQUENCE: 19

Glu Asp Trp Leu Thr Phe Gln Lys Lys His Ile Thr Asn Thr Arg Asp
 1               5                  10                  15

Val Asp Cys Asp Asn Ile Met Ser Thr Asn Leu Phe His Cys Lys Asp
```

```
                    20                  25                  30

Lys Asn Thr Phe Ile Tyr Ser Arg Pro Glu Pro Val Lys Ala Ile Cys
            35                  40                  45

Lys Gly Ile Ile Ala Ser Lys Asn Val Leu Thr Thr Ser Glu Phe Tyr
        50                  55                  60

Leu Ser Asp Cys Asn Val Thr Ser Arg Pro Cys Lys Tyr Lys Leu Lys
65                  70                  75                  80

Lys Ser Thr Asn Lys Phe Cys Val Thr Cys Glu Asn Gln Ala Pro Val
                85                  90                  95

His Phe Val Gly Val Gly Ser Cys
            100

<210> SEQ ID NO 20
<211> LENGTH: 133
<212> TYPE: PRT
<213> ORGANISM: Homo sapiens
<220> FEATURE:
<223> OTHER INFORMATION: eosinophil cationic protein (ECP)

<400> SEQUENCE: 20

Arg Pro Pro Gln Phe Thr Arg Ala Gln Trp Phe Ala Ile Gln His Ile
1               5                   10                  15

Ser Leu Asn Pro Pro Arg Cys Thr Ile Ala Met Arg Ala Ile Asn Asn
            20                  25                  30

Tyr Arg Trp Arg Cys Lys Asn Gln Asn Thr Phe Leu Arg Thr Thr Phe
        35                  40                  45

Ala Asn Val Val Asn Val Cys Gly Asn Gln Ser Ile Arg Cys Pro His
    50                  55                  60

Asn Arg Thr Leu Asn Asn Cys His Arg Ser Arg Phe Arg Val Pro Leu
65                  70                  75                  80

Leu His Cys Asp Leu Ile Asn Pro Gly Ala Gln Asn Ile Ser Asn Cys
                85                  90                  95

Arg Tyr Ala Asp Arg Pro Gly Arg Arg Phe Tyr Val Val Ala Cys Asp
            100                 105                 110

Asn Arg Asp Pro Arg Asp Ser Pro Arg Tyr Pro Val Val Pro Val His
        115                 120                 125

Leu Asp Thr Thr Ile
    130

<210> SEQ ID NO 21
<211> LENGTH: 125
<212> TYPE: PRT
<213> ORGANISM: Bos sp.
<220> FEATURE:
<223> OTHER INFORMATION: bovine angiogenin (Ang)

<400> SEQUENCE: 21

Ala Gln Asp Asp Tyr Arg Tyr Ile His Phe Leu Thr Gln His Tyr Asp
1               5                   10                  15

Ala Lys Pro Lys Gly Arg Asn Asp Glu Tyr Cys Phe His Met Met Lys
            20                  25                  30

Asn Arg Arg Leu Thr Arg Pro Cys Lys Asp Arg Asn Thr Phe Ile His
        35                  40                  45

Gly Asn Lys Asn Asp Ile Lys Ala Ile Cys Glu Asp Arg Asn Gly Gln
    50                  55                  60

Pro Tyr Arg Gly Asp Leu Arg Ile Ser Lys Ser Glu Phe Gln Ile Thr
65                  70                  75                  80
```

```
Ile Cys Lys His Lys Gly Gly Ser Ser Arg Pro Cys Arg Tyr Gly
                85                  90                  95

Ala Thr Glu Asp Ser Arg Val Ile Val Val Gly Cys Glu Asn Gly Leu
            100                 105                 110

Pro Val His Phe Asp Glu Ser Phe Ile Thr Pro Arg His
        115                 120                 125

<210> SEQ ID NO 22
<211> LENGTH: 124
<212> TYPE: PRT
<213> ORGANISM: Bos sp.
<220> FEATURE:
<223> OTHER INFORMATION: bovine seminal RNase

<400> SEQUENCE: 22

Lys Glu Ser Ala Ala Lys Phe Glu Arg Gln His Met Asp Ser Gly
 1               5                  10                  15

Asn Ser Pro Ser Ser Ser Asn Tyr Cys Asn Leu Met Met Cys Cys
                20                  25                  30

Arg Lys Met Thr Gln Gly Lys Cys Lys Pro Val Asn Thr Phe Val His
            35                  40                  45

Glu Ser Leu Ala Asp Val Lys Ala Val Cys Ser Gln Lys Lys Val Thr
    50                  55                  60

Cys Lys Asn Gly Gln Thr Asn Cys Tyr Gln Ser Lys Ser Thr Met Arg
65                  70                  75                  80

Ile Thr Asp Cys Arg Glu Thr Gly Ser Ser Lys Tyr Pro Asn Cys Ala
                85                  90                  95

Tyr Lys Thr Thr Gln Val Glu Lys His Ile Ile Val Ala Cys Gly Gly
            100                 105                 110

Lys Pro Ser Val Pro Val His Phe Asp Ala Ser Val
            115                 120

<210> SEQ ID NO 23
<211> LENGTH: 124
<212> TYPE: PRT
<213> ORGANISM: Bos sp.
<220> FEATURE:
<223> OTHER INFORMATION: bovine pancreatic RNase A

<400> SEQUENCE: 23

Lys Glu Thr Ala Ala Ala Lys Phe Glu Arg Gln His Met Asp Ser Ser
 1               5                  10                  15

Thr Ser Ala Ala Ser Ser Ser Asn Tyr Cys Asn Gln Met Met Lys Ser
                20                  25                  30

Arg Asn Leu Thr Lys Asp Arg Cys Lys Pro Val Asn Thr Phe Val His
            35                  40                  45

Glu Ser Leu Ala Asp Val Gln Ala Val Cys Ser Gln Lys Asn Val Ala
    50                  55                  60

Cys Lys Asn Gly Gln Thr Asn Cys Tyr Gln Ser Tyr Ser Thr Met Ser
65                  70                  75                  80

Ile Thr Asp Cys Arg Glu Thr Gly Ser Ser Lys Tyr Pro Asn Cys Ala
                85                  90                  95

Tyr Lys Thr Thr Gln Ala Asn Lys His Ile Ile Val Ala Cys Glu Gly
            100                 105                 110

Asn Pro Val Val Pro Val His Phe Asp Ala Ser Val
            115                 120

<210> SEQ ID NO 24
```

```
<211> LENGTH: 12
<212> TYPE: PRT
<213> ORGANISM: Artificial Sequence
<220> FEATURE:
<223> OTHER INFORMATION: Description of Artificial Sequence:N-terminus
      of rEDN

<400> SEQUENCE: 24

Met Lys Pro Pro Gln Phe Thr Trp Ala Gln Trp Phe
 1               5                  10

<210> SEQ ID NO 25
<211> LENGTH: 16
<212> TYPE: PRT
<213> ORGANISM: Artificial Sequence
<220> FEATURE:
<223> OTHER INFORMATION: Description of Artificial Sequence:N-terminus
      of (-4)rEDN

<400> SEQUENCE: 25

Met Ser Leu His Val Lys Pro Pro Gln Phe Thr Trp Ala Gln Trp Phe
 1               5                  10                  15
```